(12) United States Patent
Sarkar et al.

(10) Patent No.: US 7,537,569 B2
(45) Date of Patent: May 26, 2009

(54) METHOD AND APPARATUS FOR DETECTION OF TACHYARRHYTHMIA USING CYCLE LENGTHS

(75) Inventors: Shantanu Sarkar, Saint Paul, MN (US); David E. Ritscher, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 555 days.

(21) Appl. No.: 11/321,541

(22) Filed: Dec. 29, 2005

(65) Prior Publication Data
US 2006/0247548 A1 Nov. 2, 2006

Related U.S. Application Data

(60) Provisional application No. 60/676,227, filed on Apr. 29, 2005.

(51) Int. Cl.
*A61B 5/02* (2006.01)

(52) U.S. Cl. ...................... 600/508; 600/515

(58) Field of Classification Search .................. 607/508, 607/515, 518
See application file for complete search history.

(56) References Cited

U.S. PATENT DOCUMENTS

| | | | |
|---|---|---|---|
| 7,248,921 B2 * | 7/2007 | Palreddy et al. | ................. 607/5 |
| 2004/0092836 A1 | 5/2004 | Ritscher et al. | |

* cited by examiner

*Primary Examiner*—Carl H Layno
*Assistant Examiner*—Brian T Gedeon
(74) *Attorney, Agent, or Firm*—Stephen W. Bauer; Michael S. Soldner

(57) ABSTRACT

A multi-layer method for detecting atrial arrhythmias using ventricular cycle length information that includes performing a base layer algorithm for detecting the onset and offset of an atrial tachyarrhythmia. The multi-layer method further includes one or more higher layer algorithms executed in response to a base layer detection to confirm or reject the base layer detection. The base layer is designed to operate with high sensitivity to atrial fibrillation and/or organized atrial tachycardia and the higher layer is designed to operate with high sensitivity and high specificity to atrial fibrillation and/or organized atrial tachycardia.

16 Claims, 19 Drawing Sheets

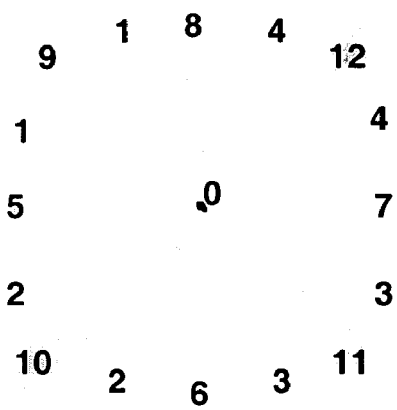
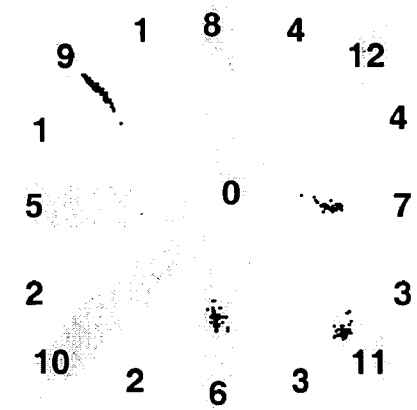
FIG. 3A  FIG. 3B
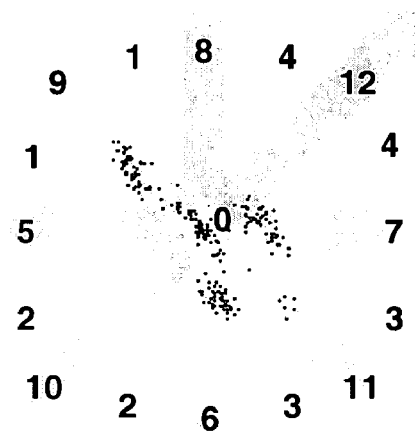
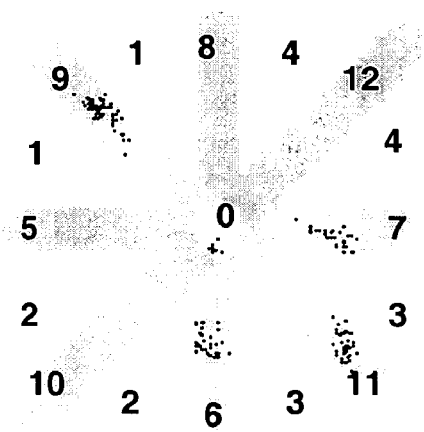
FIG. 3D  FIG. 3C
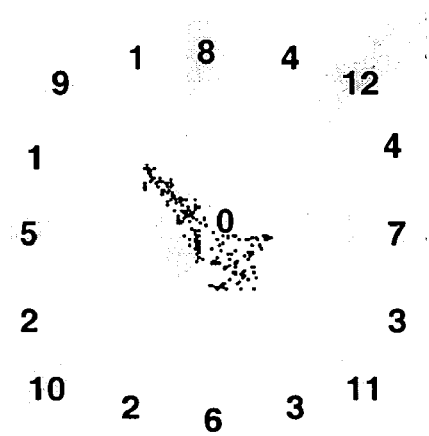
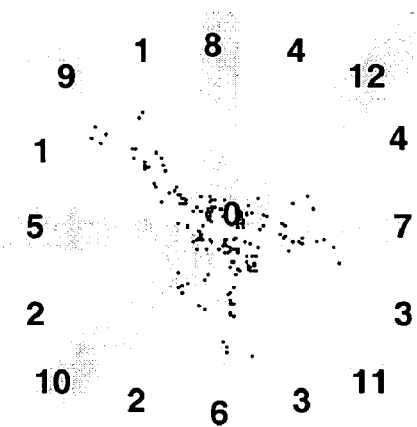
FIG. 3E  FIG. 3F

METHOD AND APPARATUS FOR DETECTION OF TACHYARRHYTHMIA USING CYCLE LENGTHS

RELATED APPLICATION

The present application claims priority and other benefits from U.S. Provisional patent application Ser. No. 60/676,227, filed Apr. 29, 2005, entitled "METHOD AND APPARATUS FOR MULTI-LAYER DETECTION OF TACHYARRHYTHMIAS," incorporated herein by reference in its entirety.

CROSS-REFERENCE TO RELATED APPLICATION

Cross-reference is hereby made to the commonly assigned related U.S. application, attorney docket number P11668.01, entitled "METHOD AND APPARATUS FOR DETECTION OF TACHYARRHYTHMIA USING CYCLE LENGTHS", to Sarkar et. al., filed concurrently herewith and incorporated herein by reference in its entirety.

FIELD OF THE INVENTION

The present invention relates to medical devices, and more particularly, to detection of arrhythmias in medical devices using discriminatory signatures of cycle lengths.

BACKGROUND OF THE INVENTION

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

During organized atrial tachycardia (OAT), including atrial flutter (AFL), the supra-ventricular rhythm is dominated by a re-entrant circuit caused by substrate changes in the atria. The effect of conduction of OAT to the AV node can result in either regular or irregular or repeating patterns of ventricular cycle lengths. The group beating patterns of ventricular cycle lengths are observed due to different levels of blocks in the proximal and distal AV node. One common pattern arises due to a 2:1 block in the proximal AV-node and a 4:3 Wenkebach block in the distal AV-node resulting in a repeating pattern of ventricular cycle lengths including two short cycles and one long cycle. Other normal and abnormal rhythms of the heart that produce variability in ventricular cycle lengths include sinus tachycardia, respiratory sinus arrhythmia, runs of premature atrial contractions (PACs) and runs of premature ventricular contractions (PVCs).

In the past, atrial arrhythmias have been largely undertreated due to the perception that these arrhythmias are relatively benign. As more serious consequences of persistent AT/AF have come to be understood, such as an associated risk of relatively more serious ventricular arrhythmias and stroke, there is a greater interest in monitoring and treating atrial arrhythmias than in the past. Furthermore, since AF and OAT typically co-exist with transitions between AF and OAT, detection and monitoring of both forms of AT are important in managing patient care, such as providing appropriate dosages of anti-coagulation therapy.

A variety of techniques have been developed for collecting and interpreting data concerning the electrical activity of the heart using external medical devices (EMDs) both in the clinical setting and by way of portable external monitors worn by an ambulatory patient or implantable medical devices (IMDs) implanted in an ambulatory patient to collect data relating to electrical heart function during daily activities of the patient.

Methods for discriminating cardiac arrhythmias have been developed for use in dual chamber implantable devices wherein both an atrial EGM signal and a ventricular EGM signal are available. Discrimination of arrhythmias can rely on atrial and/or ventricular cycle lengths, cycle length patterns, and EGM morphology. Such methods have been shown to reliably discriminate ventricular arrhythmias from supra-ventricular arrhythmias.

However, in single chamber implantable devices or in implantable or external monitoring devices, an atrial EGM signal is not always available for use in detecting and discriminating atrial arrhythmias. Detection and discrimination of AF and OAT is important, however, in properly treating the patient and preventing more serious, life-threatening or debilitating events.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein:

FIGS. 3A through 3F are Lorenz plots obtained during atrial tachycardia of varying degrees of organization, according to an embodiment of the present invention;

DETAILED DESCRIPTION

Figure 1:
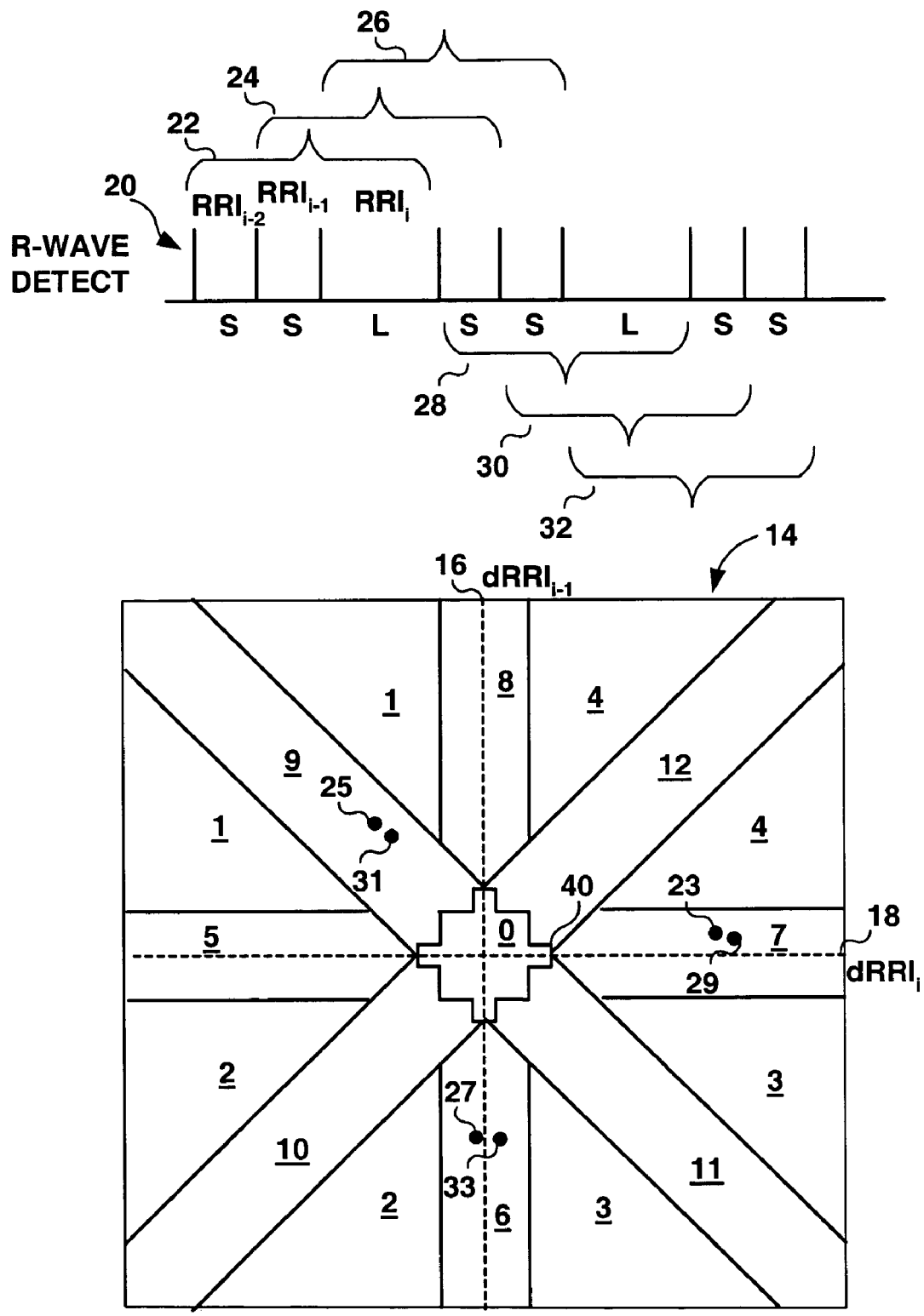
FIG. 1 is a schematic diagram of the generation of a Lorenz plot of differences between consecutive RR intervals points for a time series of RR intervals according to an embodiment of the present invention.

The present invention provides a method and apparatus for detecting and discriminating between AF and OAT using discriminatory cluster signatures of ventricular cycle lengths. The underlying conduction mechanism in the heart during AF and organized AT, as well as PACs or other causes of ventricular cycle length (VCL) irregularity, produces different patterns of irregularity in VCL. Detection and discrimination of AF and OAT, including AFL, is based on discrimination of the different patterns of VCL unique to the conduction pattern of the underlying rhythm.

The method includes acquiring ventricular cardiac signals, which could be electrical signals, pressure signals, oximetry signals, or any other physiological signal that enables a determination of ventricular cycle lengths, and measuring beat-to-beat differences in VCL. In one embodiment, electrical cardiac signals, which may be surface ECG or intracardiac EGM signals, are used to measure R-R intervals (RRIs). The difference between consecutive RRIs, or $\delta RR$, is then determined. The differences between pairs of consecutive RRIs, $\delta RR_i$ and $\delta RR_{(i-1)}$, are used to generate a two-dimensional Lorenz plot of $\delta RR_{(i-1)}$ versus $\delta RR_i$. The Lorenz plot area is divided into segments, which can be defined by a range of magnitudes and phases relative to the origin of the coordinate system. The defined segments correspond to particular VCL patterns that relate to OAT or the occurrence of PACs. During acquisition of VCL information, the Lorenz plot is represented numerically by a two-dimensional histogram wherein each segment includes a number of histogram bins. Histogram bins are used to store the ($\delta RR_i$, $\delta RR_{(i-1)}$) points determined during a set interval of time.

A number of cluster signature metrics are computed based on the number of points and the number of occupied histogram bins occurring in each segment. A regularity metric is also computed using time-scaled medians of measured RRIs. The cluster signature metrics and the regularity metric are used in a comparative analysis for detecting AF and OAT. In one embodiment, both AF and OAT are detected and discriminated using a two-dimensional histogram representation of the Lorenz plot of ($\delta RR_i$, $\delta RR_{(i-1)}$) points. In one embodiment, an algorithm is provided for AF detection only using a two-dimensional histogram of ($\delta RR_i$, $\delta RR_{(i-1)}$) points.

In yet another embodiment, a one-dimensional histogram is used for storing $\delta RR_i$ points, reducing memory requirements for performing the detection algorithm. An AF-only detection algorithm or an AF and OAT detection algorithm are provided which utilize cluster signature metrics determined from a one-dimensional representation of the Lorenz plot. In yet another embodiment, a fixed set of consecutive $\delta RR_i$ points is used in a logic based on the same principles to detect and discriminate AF from OAT.

An aspect of the invention is a multi-layer method for detecting physiological events, such as AF and/or OAT, that includes a base layer algorithm and one or more higher layer algorithms for achieving high sensitivity and high specificity of AF and/or OAT detection in a computationally efficient manner. The base layer algorithm relies on metrics that are less demanding, in terms of computational complexity, battery drain, memory requirements, etc., for detecting the onset and offset of AF and/or OAT with high sensitivity. The higher layer algorithm relies on metrics that are relatively more demanding in computational complexity, battery drain, and memory requirements for confirming or rejecting a detection made by the base layer with high sensitivity and high specificity. The higher layer algorithm requires greater computational power but is implemented at opportune times based on detections made by the base layer algorithm to achieve highly reliable AF/OAT detection with reduced computational burden. In one embodiment, the base layer and higher layer algorithms rely on evaluation of ventricular cycle length information for detecting AF and/or OAT. In particular, the higher layer algorithms may rely on cluster signature metrics determined from a histogram representation of a Lorenz plot of $\delta RR$ points.

The present invention provides methods for detecting organized tachyarrhythmia, including AFL, and AF, that rely on ventricular signals for determining VCL and do not require an atrial signal source. The methods presented may be embodied in either software or in firmware in implantable or external medical devices. Such devices include implantable monitoring devices having cardiac EGM monitoring capabilities and associated EGM sense electrodes, which may be intracardiac, epicardial, or subcutaneous electrodes. The methods provided by the present invention can also be incorporated into software or in firmware of therapy delivery for medical devices, such as a single chamber or bi-ventricular pacing system or ICD that senses the R-waves in the ventricles and delivers an electrical stimulation therapy to the ventricles, for example. Methods provided by the present invention may also be incorporated into the firmware or software of external monitors having ECG electrodes coupled to the patient's skin to detect R-waves, e.g. Holter monitors, or within computerized systems that assess pre-recorded ECG or EGM data. The invention may also be implemented in patient monitoring system, such as a centralized computer system which processes data sent to it by implantable or wearable devices.

It is also recognized that the present invention may be implemented in internal or external monitoring systems that have other sensors of ventricular activity from which VCL measurements can be made. Practice of the present invention is not limited to the use of EGM or ECG signals for measuring VCLs. Other signals, such as pressure signals, blood oximetry signals, flow signals, ventricular wall motion signals, volume-related impedance changes, or other physiological signals responsive to the ventricular cycle, can be used for measuring VCLs. Generally, VCL measurements should have a resolution on the order of about 1 to 20 ms to allow for regular patterns of VCL irregularity (as in OAT) to be discriminated from irregular patterns of VCL irregularity (as in AF) based on cluster signature metrics, however, aspects of the present invention may be implemented in systems having lower resolution of VCL measurements.

FIG. 1 is a schematic diagram of the generation of a Lorenz plot of differences between consecutive RR intervals points for a time series of RR intervals according to an embodiment of the present invention. The Lorenz plot 14 is a Cartesian coordinate system defined $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RRI_{i-1}$. $\delta RR_{i-1}$ is the difference between $RR_{i-1}$ and $RRI_{i-2}$. As such each point plotted on the Lorenz plot 14 represents a VCL pattern relating to three consecutive VCLs, $RRI_i$, $RRI_{i-1}$ and $RRI_{i-2}$. As noted previously, VCL information is not limited to detection of R-waves and determination of RRIs. The terms RRI and $\delta RR_i$ as used herein refer generally to a measurement of VCL and the difference between two consecutive VCL measurements, respectively, whether the VCL measurements were derived from a series of R-wave detections from an EGM or ECG signal or other ventricular cycle event detections from any other physiological signal. For the sake of illustration, the embodiments described herein often refer to R-wave detections for performing VCL measurements and the determination of ($\delta RR_i$, $\delta RR_{i-1}$) points.

In FIG. 1, a series of R-wave events 20 are shown. In order to plot a point on the Lorenz plot area 14, ($\delta RR_i$, $\delta RR_{i-1}$) points are determined by measuring successive RRIs determined from the R-wave events 20. In the example shown, a first series 22 of three consecutive RRIs ($RRI_{i-2}$, $RRI_{i-1}$ and $RRI_i$) presents a short-short-long VCL pattern, with the first two short RRIs being approximately equal. $\delta RR_{i-1}$, which is the difference between $RRI_{i-2}$ and $RRI_{i-1}$ is therefore approximately 0. $\delta RR_i$, the difference between the short $RRI_{i-1}$ and the relatively longer $RRI_i$, is a positive change. Accordingly, a ($\delta RR_i$, $\delta RR_{i-1}$) point 23 having a y-coordinate near 0 and a positive x-coordinate is plotted in the Lorenz plot 14, representing the short-short-long (S-S-L) sequence 22.

The next series 24 of three RRIs presents a short-long-short series resulting in a positive RRI change ($\delta RR_{i-1}$) followed by a negative RRI change ($\delta RR_i$) of approximately the same magnitude. A ($\delta RR_i$, $\delta RR_{i-1}$) point 25 having a negative x-cooridinate and a positive y-coordinate approximately equal in magnitude is plotted on the Lorenz plot 14 representing the S-L-S sequence 24. This process of plotting ($\delta RR_i$, $\delta RR_{i-1}$) points continues with the three cycle series 26 presenting a long-short-short pattern resulting in a negative $\delta RR_{i-1}$ and a $\delta RR_i$ approximately equal to zero. Point 27 is plotted in the Lorenz plot based on the negative y-coordinate and the near zero x-coordinate representing the L-S-S sequence 26.

As the pattern continues, points 29, 31, and 33 will be plotted in response to the respective S-S-L series 28, S-L-S series 30 and L-S-S series 32. The repeating pattern of S-S-L will produce clusters of plotted points corresponding to the S-S-L, S-L-S, and L-S-S repetition of the three RRI sequences. Each point plotted in the two-dimensional Lorenz plot encodes a three cycle pattern and the polarity of the changes in cycle length within the three cycle pattern. As will be described below, the resulting point cluster signatures will be used for detecting and discriminating AF and OAT. AF will result in irregular and uncorrelated VCLs and will produce a sparsely scattered plot of points as described previously in U.S. patent application Ser. No. 10/292,285, entitled "Algorithm for Detecting Arrhythmias from Discriminatory Signatures of Ventricular Cycle Lengths", filed Nov. 11, 2002. No. P10307, to Ritscher et al., incorporated herein by reference in its entirety. Varying degrees of organization during AT will result in clusters of points. In order to determine metrics of point cluster signatures, the Lorenz plot area is divided into a number of segments, labeled 0 through 12 in FIG. 1. The segments are defined based on typical point cluster signatures corresponding to OAT.

Segment 0, which includes the origin of the coordinate system, will include any points representing a series of three RRIs characterized by no change in the RRIs greater than a predefined normal sinus rhythm (NSR) RRI difference range, referred to as "NSRmask". Segment 0 extends from the origin out to a magnitude equaling NSRmask 40, and is circular in shape in an exemplary embodiment. However, an approximately square shape or other geometric shape defining a boundary approximately equal to NSRmask 40 in all directions from the origin is acceptable and will not limit the performance of an algorithm for detecting and discriminating AF from OAT. NSRmask 40 may be assigned a nominal value, e.g. 75 ms or another fixed value determined to include the range of VCL changes expected to occur during NSR due to normal autonomic modulation of the AV node. NSRmask 40 may be determined for individual patients based on historical measure of VCL variability during NSR.

Segments 1 through 12 are defined in a way that allows detection of clusters of points in plot areas and relative to one another that represent characteristic signatures of OAT. Segments 1 and 9, in the upper left quadrant of the plot area 14, will include points representing a VCL pattern of short-long-short (S-L-S). A point in segment 1 or 9 is produced by a negative $\delta RR_i$, resulting from a long $RRI_{i-1}$ subtracted from a short $RRI_i$, and a positive $\delta RR_{i-1}$, resulting from a short $RRI_{i-2}$ subtracted from a long $RRI_{i-1}$. Segment 9 will include points having $\delta RR_i$ and $\delta RR_{i-1}$ values close in magnitude indicating that the changes between the short and long VCLs are regular, as illustrated by series 24 in FIG. 1. The negative change between the L-S intervals and the positive change between the S-L intervals are nearly equal. Such S-L-S patterns of approximately equal changes in RRIs are typical of OAT during which changes in the A-V conduction ratio are occurring. The width of segment 9 is equal to NSRmask 40 to account for variation in VCLs due to autonomic modulation of the AV node.

Segment 1 will include points having differences between the short and long VCLs that vary, i.e. the negative change between the L-S intervals and the positive change between the S-L intervals in a S-L-S pattern are different. Such differences between the negative and positive changes in a S-L-S pattern are typical for rhythms presenting a compensatory pause such as PACs or PVCs.

In the opposite, lower right quadrant of plot area 14, points included in segments 3 and 11 represent VCL patterns of L-S-L. The positive change in VCL (a long $RRI_i$ minus a short $RRI_{i-1}$ resulting in a positive $\delta RR_i$) follows a negative change in VCL (a short $RRI_{i-1}$ minus a long $RRI_{i-2}$ resulting in a negative $\delta RR_{i-1}$). In segment 11, the negative change and the positive change in the L-S-L pattern are similar, typical of changing conduction ratio during OAT. The width of segment 11 is equal to NSRmask. In segment 3, the negative and positive changes are not similar in magnitude, typical of rhythms presenting a compensatory pause.

Segments 4 and 12 in the upper right quadrant of plot area 14 include points representing two positive changes in VCL presented by a pattern of short-medium-long (S-M-L). Segments 2 and 10 in the lower left quadrant include points representing two negative changes in VCL presented by a pattern of L-M-S. Points along the diagonal segments 10 and 12 will represent patterns where the two negative changes or two positive changes, respectively, are similar in magnitude, within the magnitude of NSRmask. Such patterns typically represent greater irregularity of VCL and are associated with AF or runs of premature contractions.

Segments occurring along the coordinate system axes, segments 5, 6, 7, and 8 will include points representing VCL patterns including no change and either a positive or negative change. Each of these segments also have a width equal to NSRmask to account for autonomic influences on the AV-node. Segment 5 will include points representing a change not greater than the NSRmask followed by a negative change, i.e, a pattern of L-L-S. Segment 6 will include points representing a negative change followed by a change not greater than NSRmask, i.e. a pattern of L-S-S (illustrated by series 26 and series 32 and respective points 27 and 33). Segment 7 will include points representing a change not greater than NSRmask followed by a positive change, i.e. a pattern of S-S-L (illustrated by series 22 and series 28 and respective points 23 and 29). Segment 8 will include points representing a positive change followed by a change not greater than NSRmask, i.e. a pattern of S-L-L.

Table I summarizes the VCL patterns and the corresponding relative differences in $\delta RR_i$ and $\delta RR_{i-1}$ represented by each of the segments 0 through 12 shown in FIG. 1.

TABLE I

| SEGMENT | VCL PATTERN | $\delta RR$ VALUES |
|---|---|---|
| 0 | S-S-S/L-L-L | $|\delta RR_i| <$ NSRmask |
| 1 | S-L-S | $|\delta RR_{i-1}| \neq |\delta RR_i|$ |
| 2 | L-M-S | $|\delta RR_{i-1}| \neq |\delta RR_i|$ |
| 3 | L-S-L | $|\delta RR_{i-1}| \neq |\delta RR_i|$ |
| 4 | S-M-L | $|\delta RR_{i-1}| \neq |\delta RR_i|$ |
| 5 | L-L-S | One $|\delta RR| <$ NSRmask |
| 6 | L-S-S | One $|\delta RR| <$ NSRmask |
| 7 | S-S-L | One $|\delta RR| <$ NSRmask |
| 8 | S-L-L | One $|\delta RR| <$ NSRmask |
| 9 | S-L-S | $|\delta RR_{i-1}| \approx |\delta RR_i|$ |
| 10 | L-M-S | $\delta RR_{i-1} \approx |\delta RR_i|$ |
| 11 | L-S-L | $|\delta RR_{i-1}| \approx |\delta RR_i|$ |
| 12 | S-M-L | $\delta RR_{i-1} \approx |\delta RR_i|$ |

Figure 2A:
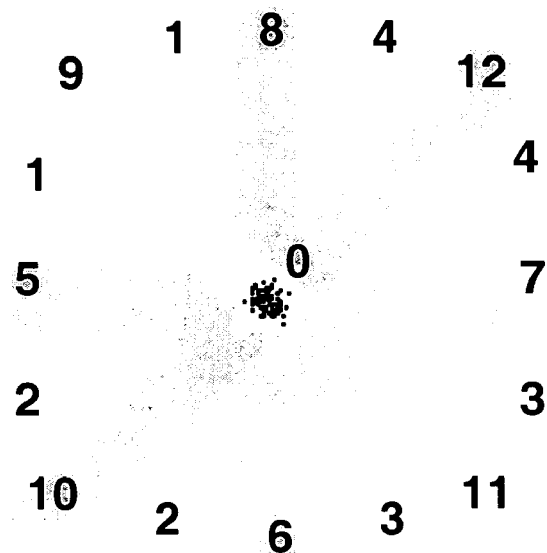
FIGS. 2A and 2B are Lorenz plots obtained during normal sinus rhythm and during atrial fibrillation, respectively, according to an embodiment of the present invention.
Figure 2B:
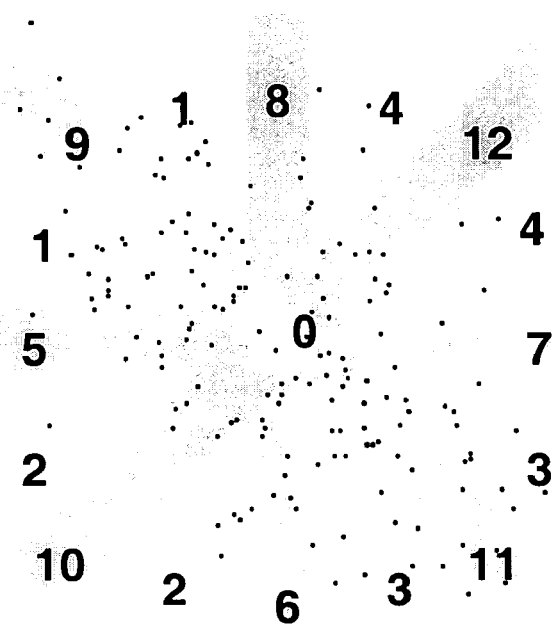

The VCL pattern sequence and corresponding $\delta RR$ relations corresponding to segments 0 through 12 shown in FIG. 1. FIGS. 2A and 2B are Lorenz plots obtained during normal sinus rhythm and during atrial fibrillation, respectively, according to an embodiment of the present invention. In both plots, a two-minute segment of $\delta RR_{i-1}$ is plotted versus $\delta RR_i$. During NSR, as shown in FIG. 2A, the plotted points are tightly clustered within NSRmask 40, in segment 0. During AF, as shown in FIG. 2B, the ($\delta RR_i$, $\delta RR_{i-1}$) points are sparsely scattered over the plot area with points falling into each of the segments 0 through 12. The VCLs are irregular and uncorrelated.

FIGS. 3A through 3F are Lorenz plots obtained during atrial tachycardia of varying degrees of organization, according to an embodiment of the present invention. The plots are generated from two-minute segments of RRIs during varying degrees of organization. FIG. 3A represents OAT with very regular VCLs due to regular atrial activations with consistent 1:1 A-V node conduction. The only variations of VCL are the result of autonomic modulation of the A-V node. FIGS. 3B through 3D show different degrees of discrete organization with clusters of points in segments 6, 7, 9 and 11. These examples represent a common cluster signature of OAT with regularly irregular VCLs due to discretely inconsistent A-V node conduction. The density or sparseness of each cluster suggests varying degrees of autonomic modulation of the A-V node.

FIGS. 3E and 3F represent OAT with a greater degree of irregularity of VCLs as a result of irregular atrial activations and inconsistent AV node conduction. Variation in VCLs occurs to varying degrees during AT depending on modulation of refractoriness of the A-V node by irregular atrial activation, autonomic modulation of the A-V node, and changes in A-V conduction ratio.

FIG. 3B represents the greatest degree of organization and FIG. 3F represents the least organization for the examples shown. FIGS. 3A through 3F suggest a continuum of organization exits in which all possible changes in A-V conduction ratio and A-V node modulation by the autonomic nervous system are possible. Each of these examples also illustrate that during OAT, there is a high probability that points will exist in segments 6, 7, 9 and 11. Each cluster indicates a discrete change in A-V conduction ratio. The density of point clusters will vary with varying degrees of autonomic modulation of the A-V node. AF and OAT detection algorithms can exploit these recognizable patterns of VCL changes by quantifying the cluster signatures using a number of cluster signature metrics.

Figure 4A:
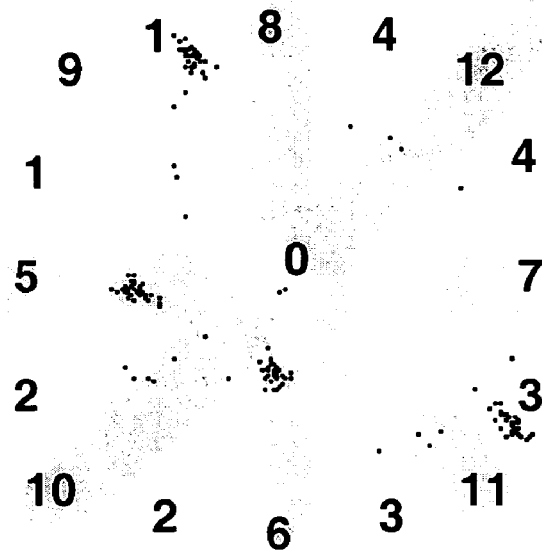
FIGS. 4A and 4B are Lorenz plots obtained during runs of premature atrial contractions (PACs) according to an embodiment of the present invention.
Figure 4B:
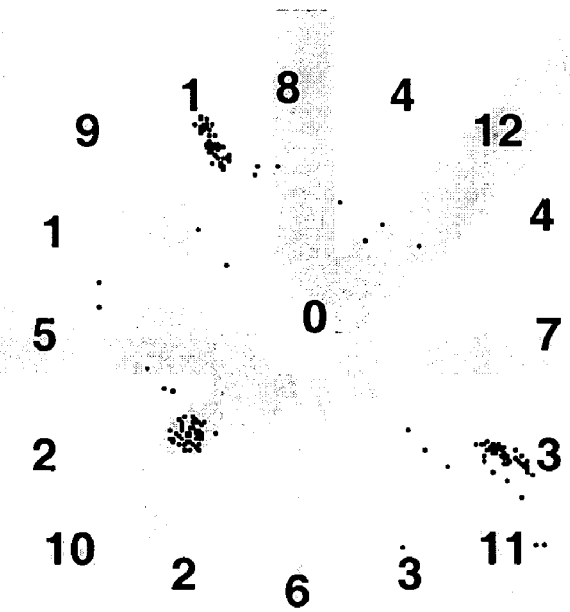

FIGS. 4A and 4B are Lorenz plots obtained during runs of premature atrial contractions (PACs) according to an embodiment of the present invention. In FIG. 4A, clusters of points in segments 1 and 3 and segments 5 and 6 result from the presentation of bigeminy (two rapid beats followed by a compensatory pause) during a run of PACs. In FIG. 4B, clusters of points in segments 1 and 3 and in segment 10 result from the presentation of trigeminy (three rapid beats followed by a compensatory pause) during a run of PACs. Point clusters in the off-diagonal segments of 1 and 3 are common during runs of PACs.

Based on observations such as these, a number of cluster metrics can be defined for providing a comparative analysis of the location of points and point clusters and the relative sparseness or density of point clusters in a Lorenz plot. These cluster metrics can then be evaluated for discriminating AF from OAT.

Figure 5:
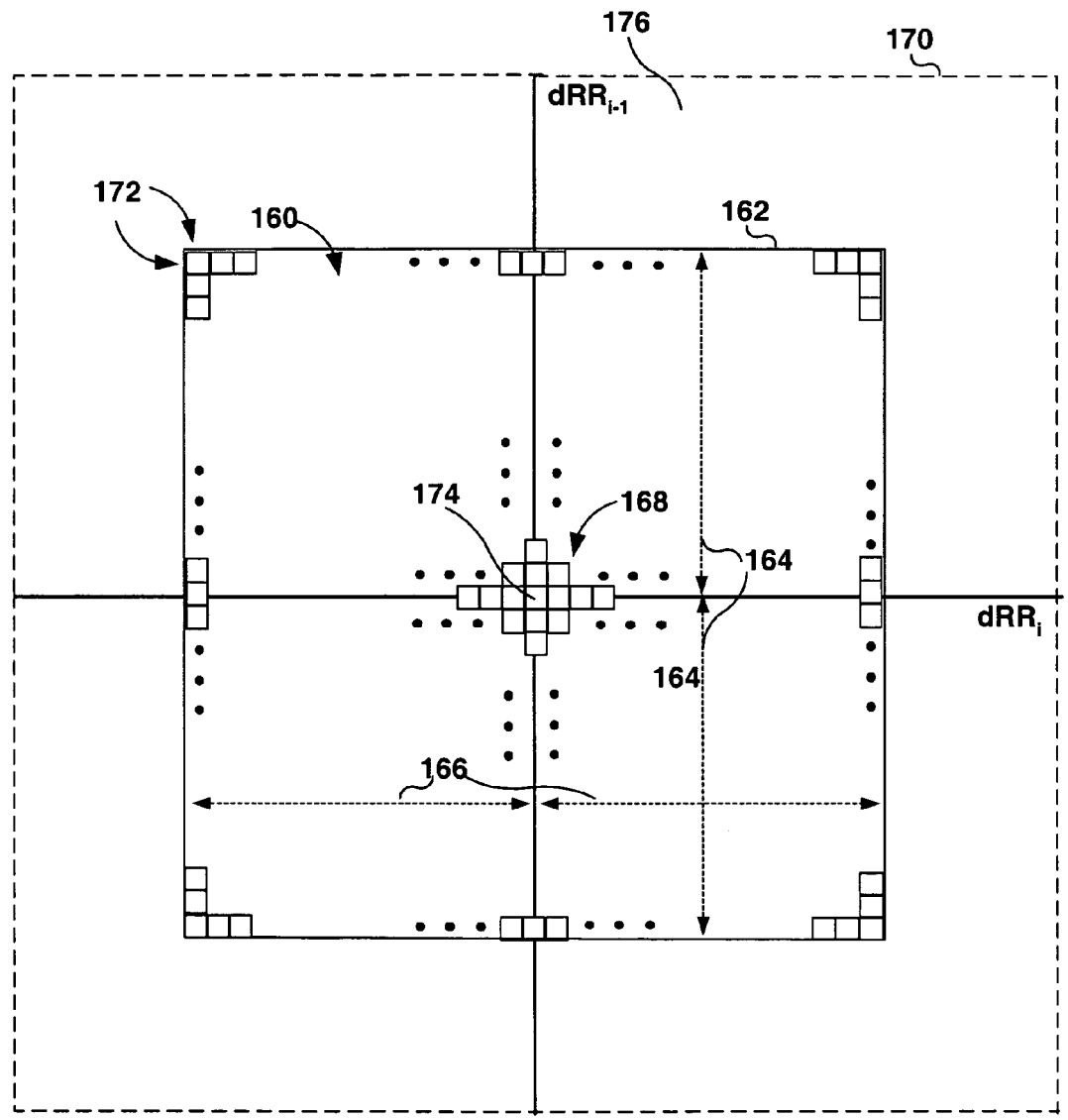
FIG. 5 is a two-dimensional histogram of the Lorenz plot area according to an embodiment of the present invention.

FIG. 5 is a two-dimensional histogram of the Lorenz plot area according to an embodiment of the present invention. The Lorenz plot area is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In one example, the histogram range may extend from −1200 ms to +1200 ms for both $\delta RR_i$ and $\delta RR_{i-1}$ values, and the histogram range is divided into bins extending 7.5 ms in each of the two dimensions resulting in a 160×160 histogram.

An outlier boundary 170 is defined. Any ($\delta RR_i$, $RR_{i-1}$) values outside the outlier boundary 170 are ignored for purposes of determining cluster signature metrics. In one embodiment, the outliers are any points having coordinate values less than −1,500 ms or greater than +1,500 ms. Outlier points are not counted in the two-dimensional histogram bins.

Out-of-range points may defined as points having ($\delta RR_i$, $\delta RR_{i-1}$) coordinates falling outside the histogram range 162 but within the outlier boundary 170. For example, if the two-dimensional histogram 160 has a range 162 of ±600 ms in each $\delta RR_i$ and $\delta RR_{i-1}$ direction and the outlier boundary 170 is defined as ±1,500 ms, a point defined by ($\delta RR_i$, $\delta RR_{i-1}$) is an outlier if $\delta RR_i$ or $\delta RR_{i-1}$ is outside the histogram range 162 (±1200 ms) but within the outlier boundary 170 (±1,500 ms). Points falling in the out-of-range zone 176 can be counted in the appropriate "edge" bin selected along the outer range 172 of the two-dimensional histogram 162. In other embodiments, out-of-range points may be ignored and not counted in a histogram bin.

An origin bin 174 is defined as the bin containing the origin of the Lorenz plot area. During highly organized AT, or AFL, as shown in FIG. 3A, the origin bin 174 will contain a large percentage of the ($\delta RR_i$, $\delta RR_{i-1}$) points. The two-dimensional histogram illustrated in FIG. 5 is used to quantify the number and relative location of ($\delta RR_i$, $RR_{i-1}$) points determined from measured VCLs such that a number of cluster signature metrics can be derived for use in discriminating AF and OAT. In some embodiments, one or both of the ($\delta RR_i$, $\delta RR_{i-1}$) coordinates are multiplied by a factor $k_i$ or $k_{i-1}$, respectively, prior to storing the point in the two-dimensional histogram. In one example, the $\delta RR$ value is multiplied by a value of k=2 if one of the VCLs used to compute $\delta RR$ is less than 500 ms. The $\delta RR$ value is multiplied by a value of k=0.5 if one of the VCLs used to compute $\delta RR$ is greater than 1000 ms. In the discussion that follows, reference to a ($\delta RR_i$, $\delta RR_{i-1}$) point can also refer to a ($k_i*\delta RR_i$, $k_{i-1}*\delta RR_{i-1}$) point in which the point coordinate values have been adjusted by a factor $k_i$ or $k_{i-1}$.

Multiplication of the $\delta RR$ values by a constant enables efficient use of a fixed histogram range and bin sizes. The variability of R-R intervals is generally small at very fast rates producing a relatively dense cloud of points over a small range of histogram bins. At lower tachyarrhythmia rates, the $\delta RR$ values are relatively larger producing more sparse Lorenz plot points over a larger range of the plot area. Multiplication of the small $\delta RR$ values by a constant and dividing larger $\delta RR$ values by the constant allows a fixed histogram range and bin size to be used effectively for measuring cluster signature metrics.

In some embodiments, the two-dimensional histogram is defined by fixed parameters. In other embodiments, the histogram parameters (such as histogram range and bin size) can be dynamic based on some characteristic of the VCL data stream. For example, the histogram range and bin size may be defined as functions of the VCL median during a data acquisition time interval. As the median VCL changes, a new histogram range and bin size can be determined. Other aspects of the VCL data stream, such as the VCL range, average, or standard deviation, could be used for defining variable histogram parameters.

Figure 6:
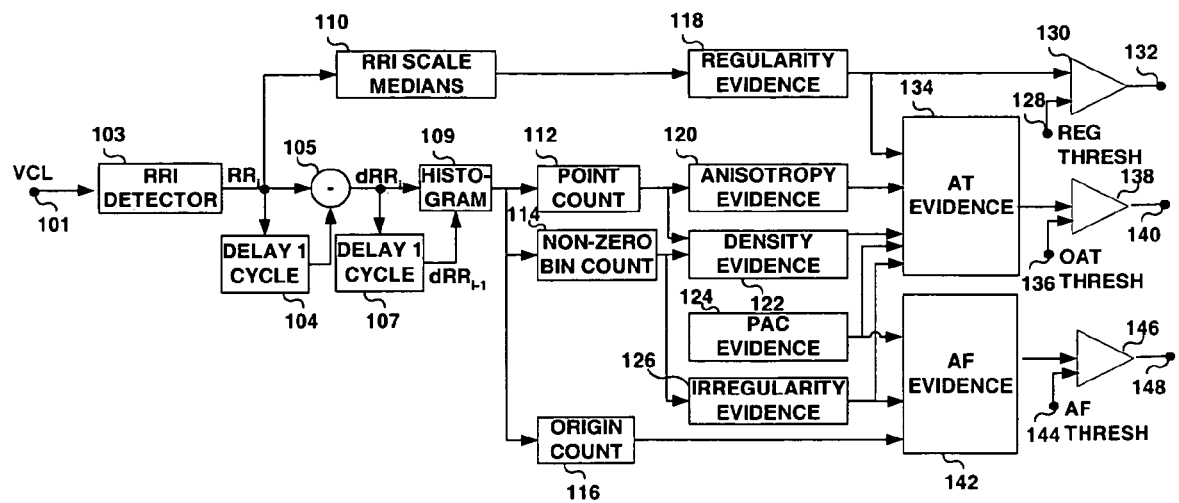
FIG. 6 is a functional block diagram of an apparatus used for detecting and discriminating atrial fibrillation and organized atrial tachycardia using a numerical, two-dimensional histogram representation of a Lorenz plot of ventricular cycle lengths according to an embodiment of the present invention.

FIG. 6 is a functional block diagram of an apparatus used for detecting and discriminating atrial fibrillation and organized atrial tachycardia using a numerical, two-dimensional histogram representation of a Lorenz plot of ventricular cycle lengths according to an embodiment of the present invention. The functions summarized in FIG. 6 can be implemented in an implantable medical device such as a cardiac stimulation device, including pacemakers and implantable cardioverter defibrillators, or cardiac monitoring device. An example of an implantable monitoring device in which the present invention may be incorporated is disclosed in U.S. Pat. No. 5,987,352 issued to Klein, et al., hereby incorporated herein by reference in its entirety. Alternatively, the functions summarized in FIG. 6 may be implemented in an external device used for monitoring heart rhythms. In other embodiments, the functionality summarized in FIG. 6 may be implemented across more than one device. For example, an implantable medical device may be used to obtain EGM signals for collecting and storing RRI data that is uplinked to an external device for analysis and evaluation. A variety of device implementations may be realized for achieving AF and OAT detection and discrimination according to the functions summarized by FIG. 6.

A VCL signal source 101 is provided as input to an RRI detector 103. VCL signal source 101 is provided as any physiological signal containing ventricular cycle information such that VCLs may be derived there from. VCL signal source 101 may be embodied as cardiac or surface electrodes for sensing electrical signals of the heart, including R-wave signals. RRI detector 103 detects the R-waves, or another event indicative of the onset of the ventricular cycle, from the signal received from VCL signal source 101 and provides an RRI signal as output. In one embodiment, RRI detector 103 includes a sense amplifier for detecting R-waves based on an automatically adjusting R-wave detection threshold. Each time an R-wave is detected an R-wave detection signal is generated and the time interval occurring between R-wave detection signals is provided as output from RRI detector 103.

The present invention is not limited to the use of an ECG/EGM signal for detecting RRIs. The concept of RRI can be generalized to any VCL; it is the activation of the ventricles that is of interest, not the specifics of the electrical activation. Other physiological signals could be substituted for VCL signal source 101 from which an approximation of the start of the ventricular cycle can be made. In one alternative embodiment, a pressure signal may be used to detect the start of the cardiac cycle. For example, a predetermined threshold crossing of pressure amplitude or dP/dt amplitude may be detected as a ventricular activation-related event and used as the starting point of a ventricular cycle for the purposes of measuring VCLs by RRI detector 103. Alternative cardiac signal sources for use in measuring VCLs include a ventricular pressure signal, wall motion signal, blood oximetry signal or other signal characterized by cyclic fluctuations corresponding to ventricular cycle lengths. A feature of the VCL signal source 101 corresponding to the start of the ventricular cycle is detected by 'RRI' detector 103 for measuring ventricular cycle lengths. Any known method for measuring ventricular cycle lengths may be used by RRI detector 103.

The output of RRI detector 103 is provided to a scale median RRI module 110. Scale median RRI module 110 computes the median RRI for a number of different time scales. During AT having any degree of organization, an underlying base VCL will exist which becomes regularly irregular due to changes in the AV node conduction ratio. The median RRI determined from varying time intervals will be consistent when the base VCL is present during OAT. By determining the median RRI over different time scales and comparing these "scale medians", a determination of the regularity of VCLs can be made. As such, a metric of VCL regularity, named RegularityEvidence, can be computed at block 118 using the scale medians received as input from Median RRI module 110.

Figure 7:
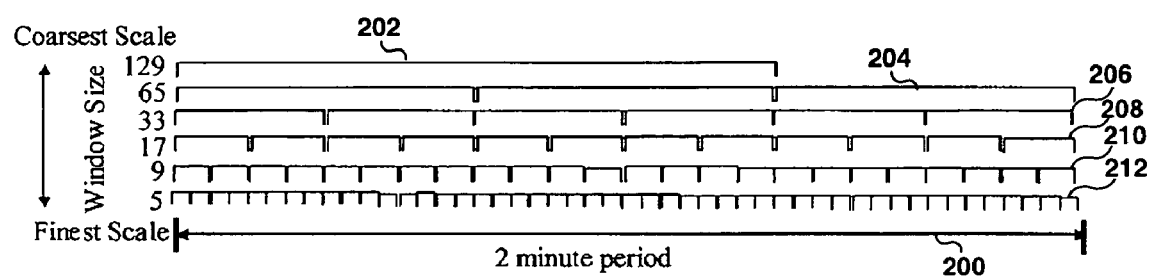
FIG. 7 is a time line for determining RR interval scale medians according to an embodiment of the present invention.

FIG. 7 is a time line for determining RR interval scale medians according to an embodiment of the present invention. Generally, a number of differently-sized sample windows 202, 204, 206, 208, 210, and 212 are acquired during a predetermined interval of time 200 for computing scale medians. The sample windows may be defined according to sample size or according to an interval of time. The RRI median is determined for each time scale or sample number scale window. In one embodiment, sample number scale windows of $2^n+1$ are taken over a T minute time interval. In the example shown in FIG. 7, sample number window sizes of 5, 9, 17, 33, 65, and 129 are applied over a 2 minute time interval. The medians for all the time or sample number scales may be used or the medians for a selected set of scales may be used. The number of RRIs occurring during the 2 minute interval will determine the number of 5-sample windows, 9-sample windows, 17-sample windows, etc. that can be obtained. Each sample window is repeated until the T-minute interval 200 expires. During each sample window, an RRI median is determined from the $2^n+1$ samples. The median RRI for the T-minute interval is also determined.

The RegularityEvidence metric computed by module 118 using the scale medians provided by RRI scale medians module 110 can be computed as the percentage of scale medians that are within a predetermined range of a baseline RRI median. The baseline RRI median is a RRI median determined from a previous time window. In an exemplary embodiment the baseline RRI median is determined as the median of the previous time interval, T. In alternative embodiments, a baseline RRI median may be determined from any selected preceding time interval or may be a running median RRI that is updated on a beat-by-beat or other periodic basis.

Figure 8:
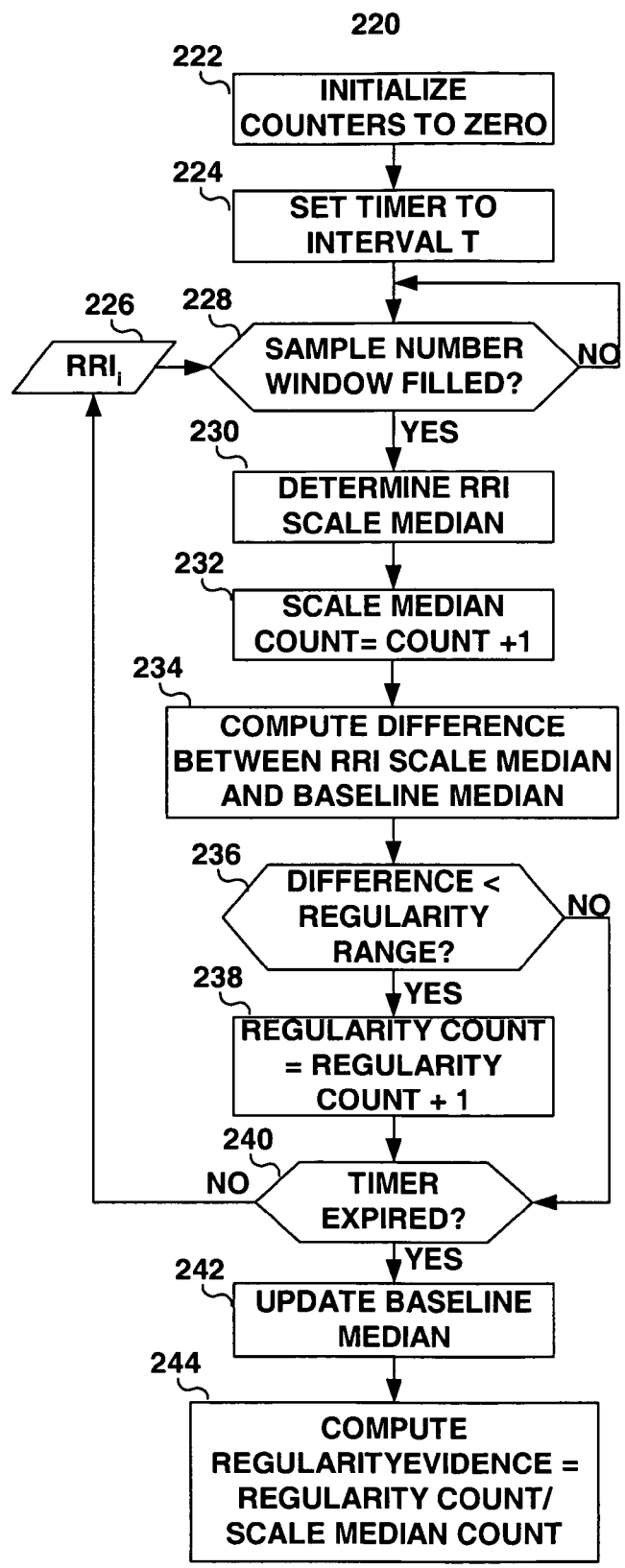
FIG. 8 is a flow chart of a method for computing a metric using RR interval scale medians according to an embodiment of the present invention.

FIG. 8 is a flow chart of a method for computing a metric using RR interval scale medians according to an embodiment of the present invention. Method 220 begins at step 222 by initializing counters to zero that will be used in counting the number of RRI medians computed during a time interval, T, and the number of RRI medians that are within a regularity range of the baseline RRI median.

At step 224, a timer is set to the predetermined time interval, T, over which a number of scale median RRIs will be determined. RRIs are provided as input at step 226. RRIs measured by RRI detector 103 (FIG. 6) are stored in a temporary memory buffer for determining the scale median RRIs. In the exemplary embodiment provided above, $2^n+1$ where n=2, 3, 4, 5, 6, and 7 RRIs are stored to fill sample number windows of 5, 9, 17, 33, 65 and 129 RRIs. In alternative embodiments, RRIs provided as input at step 226 may be stored over a number of time scale windows. For example, RRIs may be stored for intervals of 5, 10, 20, 40, 60 and 120 seconds. Each sample number or time scale window is repeated over the interval T until T expires. As such, each time a sample number window is filled with the desired number of samples or when a time scale window expires, prior to expiration of T, as determined by decision step 228, an RRI scale median is determined at step 230. A counter used to count the number of scale medians computed during time interval T is increased by 1 at step 232 each time a scale median is determined at step 230.

At step 234, the difference between the RRI scale median and the baseline median is computed. In an exemplary embodiment, the baseline median is the RRI median determined for the previous time interval T. The difference between the RRI scale median and the baseline median is compared to the regularity range at decision step 236. The regularity range is set to a time interval that is expected to encompass VCL variability during highly organized AT, such as AFL, or discreet OAT during varying A-V conduction ratios. As seen in the example of FIG. 3A, a tight cluster of points are presented in segment 0 during highly organized AT or AFL due to small variability of VCL during a constant AV conduction ratio. In the example of FIG. 3B, tight clusters of points are presented in different segments due to small variability in VCL occurring during changes in A-V conduction ratio. In one embodiment, the regularity range is set to ±12 ms. The regularity range does not encompass the variability of VCL that is expected during NSR as seen in FIG. 2A.

If the difference between the scale median determined at step 230 and the baseline median is less than 12 ms or another selected regularity range, the scale median is considered to be representative of regular VCLs that occur during highly organized AT. A regularity counter is increased by one at step 238. If the difference between the scale median and the baseline median is greater than the selected regularity range, the scale median is considered to be representative of VCL variability that occurs during NSR or VCL irregularity that occurs during AF. The regularity count is not increased at step 238 if the difference is not within the regularity range.

At step 240, method 220 determines if the time interval T has expired. If not, method 220 continues to store RRIs at input step 226 for computing scale medians as the scale median windows are filled or expired. If time interval T has expired at decision step 240, the baseline median can be updated at step 242. When the baseline median is defined as the median of the previous time interval T, a new baseline median is determined at the expiration of each time interval T to be used in comparisons with scale medians determined during the next time interval T.

At step 244, the RegularityEvidence is computed as the percentage or ratio of the regularity count to the total number of scale medians determined, or the scale median count. During highly organized AT (as shown in FIG. 3A), RegularityEvidence will have a value equal to or approaching 1, with all scale medians within the regularity range of the baseline median. During AF, RegularityEvidence will have a value equal to or approaching 0. RegularityEvidence will have an intermediate value between 0 and 1 during NSR and varying degrees of OAT.

Referring again to the functional block diagram of FIG. 6, the RegularityEvidence metric computed at block 118 is provided as input to regularity comparator 130. RegularityEvidence can be used in the detection of OAT by comparing RegularityEvidence to a regularity threshold 128, also provided as input to regularity comparator 130. If RegularityEvidence exceeds the regularity threshold 128, OAT is detected and an OAT detection signal 132 is generated by comparator 130. The regularity threshold 128 is selected such that the comparison made by regularity comparator 130 is sensitive to the detection of tight clusters of points in segment 0 representative of highly organized AT (as shown in FIG. 3A) and does not detect a more sparse cluster signature in segment 0 representative of NSR (as shown in FIG. 2A).

The output of RRI detector 103 is also provided as input to subtraction block 105 and to a temporary buffer 104 for storing the RRI for one ventricular cycle. The previous RRI ($RR_{i-1}$) stored by buffer 104 and the new RRI are provided as input to subtraction block 105 such that the difference in two consecutive RRIs, or $\delta RR_i$, can be computed and provided as input to Histogram counter 109. Output $\delta RR_i$ from subtraction block 105 is also provided as input to temporary buffer 107 for storing $\delta RR_i$ for one ventricular cycle such that the previous $\delta RR_i$, or $\delta RR_{i-1}$, is provided with the new $\delta RR_i$ as input to Histogram counter 109. Upon receiving the ($\delta RR_i$, $\delta RR_{i-1}$) values, Histogram counter 109 updates the histogram bin count corresponding to the ($\delta RR_i$, $\delta RR_{i-1}$) value. Thus Histogram counter 109 includes a number of counters corresponding to each histogram bin included in the two-dimensional histogram 162 shown in FIG. 5. Histogram counter 109 is not required for all implementations of the present invention in that counting only the number of points and the number of occupied bins in each segment can be sufficient for determining a number of cluster signature metrics without a complete count of all histogram bins.

Upon updating the appropriate histogram bin counter, a number of other counts are updated according to the histogram bin that contained the new ($\delta RR_i$, $\delta RR_{i-1}$) point. PointCount$_n$ counter 112 is used to count the number of points counted in bins within each of the n segments of the Lorenz plot area, for example segments 0 through 12 as shown in FIG. 1, to generate a total number of points in each segment. As such PointCount$_n$ counter 112 includes a segment point counter for each of the n defined segments, one of which is appropriately increased each time a new ($\delta RR_i$, $\delta RR_{i-1}$) point causes a histogram bin to be increased.

The NonZeroBinCount$_n$ counter 114 is used to count the number of occupied bins within each segment of the Lorenz plot area to generate a total number of segments having a point located therein. As such, NonZeroBinCount$_n$ counter 114 includes n counters, each of which correspond to one of the n segments defined in the Lorenz plot area. If a new ($\delta RR_i$, $\delta RR_{i-1}$) point is counted by a previously unoccupied bin by Histogram counter 109, a counter within NonZeroBinCount$_n$ counter 114 that corresponds to the segment containing the previously unoccupied bin is increased by one.

OriginCount counter 116 is used to count the number of points falling in the origin bin 174 (shown in FIG. 5). If a new ($\delta RR_i$, $\delta RR_{i-1}$) point causes an increment of the origin bin by Histogram counter 109, OriginCount counter 116 is increased by one. Thus, each time a new ($\delta RR_i$, $\delta RR_{i-1}$) point is counted by Histogram counter 108, three additional counters, PointCount$_n$ counter 112, NonZeroBinCount$_n$ counter 114, and OriginCount counter 116 are updated as appropriate.

At the end of a predetermined data acquisition time interval, the counter values are used to determine a number of cluster signature metrics. The data acquisition time interval may be set to a number of seconds or minutes. In an exemplary embodiment, the data acquisition time interval is set to 2 minutes such that counters 112, 114, and 116 are updated on every cardiac cycle during the 2 minute interval, and, at the end of the 2 minute interval, the cluster signature metrics are determined, including the RegularityEvidence metric described above. All the counters are reset to zero after computation of the cluster signature metrics at the end of the data acquisition interval.

At block 120, an AnisotropyEvidence metric is computed. The AnisotropyEvidence metric is used to recognize a directionality of cluster patterns typical of discrete organization of AT during varying conduction ratios as observed in the example Lorenz plots shown in FIGS. 3B through 3F. The PointCount values corresponding to segments 5, 6, 7, 8, 9, 10, and 11 are obtained from PointCount$_n$ counter 112. A high number of points in diagonal segments 9 and 11 and axial segments 6 and 7 relative to the number of points in diagonal segments 10 and 12 and axial segments 5 and 8 (shown in FIG. 1) will be indicative of a OAT cluster signature, for example as shown in FIGS. 3B through 3F.

Figure 9:
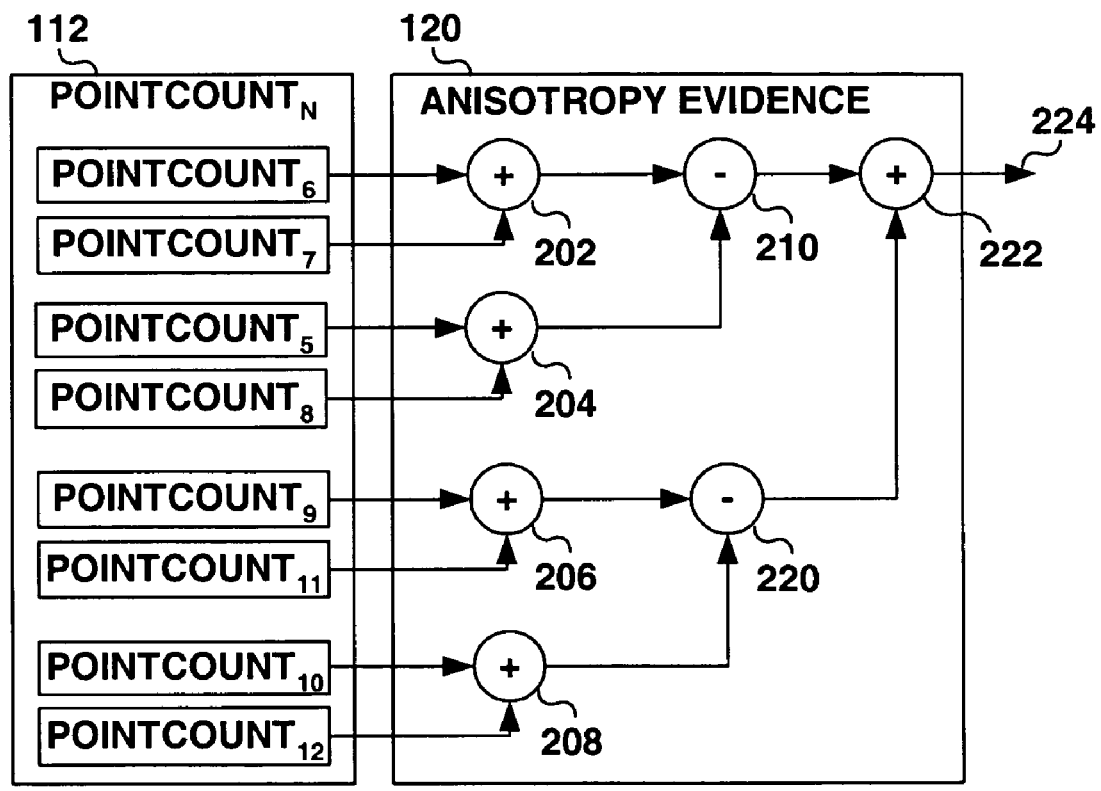
FIG. 9 is a functional block diagram of the computation of an anisotropy metric according to an embodiment of the present invention.

FIG. 9 is a functional block diagram of the computation of an anisotropy metric according to an embodiment of the present invention. The number of points counted in bins found in segments 5 and 8 (PointCount$_5$ and PointCount$_8$) are provided as input to summation block 204 The resulting sum is provided to subtraction block 210. The values of PointCount$_6$ and PointCount$_7$ are provided as input to summation block 204 and the resulting sum is provided to subtraction block 210 such that the difference between the number of points in segments 6 and 7 and the number of points in segments 5 and 8 can be determined to identify an anisotropic signature.

Likewise, the values of PointCount$_9$ and PointCount$_{11}$ are provided as input to summation block 206 and the resulting sum is provided to subtraction block 220. The values of PointCount$_{10}$ and PointCount$_{12}$ are provided as input to summation block 208 and the resulting sum is provided to subtraction block 220 such that the difference between the number of points in segments 9 and 11 and the number of points in segments 10 and 12 can be determined to identify an anisotropic signature.

The absolute values of the outputs of subtraction block 210 and subtraction block 220 are summed at summation block 222 to provide AnisotropyEvidence output 224 as a metric of anisotropy.

The computation of AnisotropyEvidence by module 120 is presented mathematically by the following equation:

$$AnisotropyEvidence = \left| \sum_{n=9,11} PointCount_n - \sum_{n=10,12} PointCount_n \right| + \left| \sum_{n=6,7} PointCount_n - \sum_{n=5,8} PointCount_n \right|$$

AnisotropyEvidence will be 0 during normal sinus rhythm and during highly organized AT as shown in FIG. 3A since the point counts for segments 5 through 12 will be 0. AnisotropyEvidence will be a high value during OAT of the type shown in FIG. 3B and will marginally decrease in value for the OAT examples shown in FIGS. 3C through 3F. AnisotropyEvidence will have a low, non-zero value during AF.

Referring again to the functional block diagram of FIG. 6, at block 122 DensityEvidence is computed as a metric of the density of points plotted in each segment. DensityEvidence is an indication of the group beating phenomenon associated with different A-V conduction ratios during OAT. The density of points in a given segment, Density$_n$, can be measured by computing the difference between the number of points in the segment and the number of occupied bins in the segment:

Density$_n$=PointCount$_n$−NonZeroBinCount$_n$

If the point density is high, a relatively large number of points will occupy a small number of bins, resulting in a high value for Density$_n$. If the points are sparse, as in the case of AF, the points in any given segment will be spread across a relatively large number of bins resulting in a low value for Density$_n$.

DensityEvidence is computed at block 122 as the summation of the Density values for segments 5 through 12, which typically contain point clusters associated with OAT:

$$DensityEvidence = \sum_{n=5\,to\,12} Density_n$$

The most sparse ($\delta RR_i$, $\delta RR_{i-1}$) point distribution, as found during AF, will result in a DensityEvidence equal to, or close to, 0. The number of points will approach, or be equal to, the number of occupied bins. DensityEvidence will also be equal or close to 0 during NSR since both the point count and the number of occupied bins in segments 5 through 12 will be 0, with all or most points falling in segment 0. The highest density in any given segment will occur when all the points fall into a single bin, resulting in Density$_n$ equal to the number of points minus 1 (PointCount$_n$–1). If the Density$_n$ values for one or more of segments 5 through 12 is high, then the metric DensityEvidence will be high providing evidence of OAT. Considering the examples shown in FIG. 3B through 3F, DensityEvidence will be highest for the OAT shown in FIG. 3B and decrease for the examples shown through FIG. 3F.

At block 124, a metric for determining the evidence of PACs, PACEvidence, is computed. As seen in the examples shown in FIGS. 4A and 4B, cluster signatures associated with runs of PACs typically present a cluster of points in segments 1, 2, 3 or 4 along with a cluster of points in either segment 10 with none or a few points in opposing segment 12 (FIG. 4B), or in segments 5 and 6, with few points in opposing segments 7 and 8. As such, PACEvidence is computed as the summation of the Density$_n$ values for segments 1 through 4, added to the difference between the sum of Density$_n$ values for segments 5 and 6 and the sum of Density$_n$ values for segments 7 and 8, added to the difference between the Density$_n$ values of segment 10 and segment 12:

$$PACEvidence = \sum_{n=1,2,3,4,5,6,10} Density_n - \sum_{n=7,8,12} Density_n$$

At block 126, a metric of VCL irregularity, IrregularityEvidence, is computed. An increasing number of bins outside the 0 segment will be filled with increasing VCL irregularity. The irregularity metric is therefore computed as the number of occupied bins, i.e., the sum of all NonZeroBinCount values, for all segments except the 0 segment:

$$IrregularityEvidence = \sum_{n=1 \, to \, 12} NonZeroBinCount_n$$

IrregularityEvidence will be 0 for NSR and for the example of highly organized AT as shown in FIG. 3A since all points will fall in segment 0. IrregularityEvidence will be high during AF (see FIG. 2B) and have varying non-zero values representative of the degree of VCL irregularity during OAT. With regard to the examples shown in FIGS. 3B through 3F, IrregularityEvidence will be lowest during the OAT episode represented by FIG. 3B and will be increasing in value for the episodes shown through FIG. 3F.

The cluster signature metrics for anisotropy, density, PACs, regularity and irregularity are provided as input to compute a metric for detecting OAT at block 134. The cluster signature metrics for PACs and irregularity and OriginCount are provided as input to a metric for use in detecting AF at block 142. Regular VCL irregularity, anisotropic patterns of ($\delta$RRi, $\delta$RRi-1) points, and density or clustering of ($\delta$RR$_i$, RR$_{i-1}$) points unrelated to runs of PACs are evidence of OAT. In one embodiment, ATEvidence metric is computed from the cluster signature metrics according to the following equation:

ATEvidence=IrregularityEvidence+DensityEvidence+ AnisotropyEvidence+RegularityEvidence– K*PACEvidence The constant K is selected as a weighting value for PACEvidence. A nominal value for K is 4 such that the PACEvidence metric can offset the other four cluster signature metrics that provide evidence of AT. In other embodiments, other weighting factors could be selected for each of the cluster signature metrics used in computing ATEvidence. In the equation shown above for computing ATEvidence, a nominal set of weighting factors of {1, 1, 1, 1, –4} can be used. However, weighting factors applied to each of the terms in the ATEvidence equation can be optimized to any value, including 0, for providing a sensitive and specific metric for the detection of AT.

Irregular VCL irregularity is evidence of AF. A high OriginCount would be evidence against AF. As such, AFEvidence is computed from the cluster signature metrics according to the following equation:

AFEvidence=IrregularityEvidence–OriginCount– J*PACEvidence

The constant J is selected as a weighting value for PACEvidence which may be a different value than used as the weighting coefficient in computing AFEvidence. A nominal value for J is two. Weighting factors may also be applied to the other terms included in the AFEvidence equation. The IrregularityEvidence metric alone could be used for detecting AF. As such, a weighting factor for OriginCount could be zero. However, by including OriginCount in the AFEvidence equation, AF detection may be made with greater sensitivity. Weighting factors that have been optimized for high specificity and high sensitivity of AF detection can be applied to each of the terms in the AFEvidence equation provided above.

The ATEvidence metric and the AFEvidence metric are provided as inputs to comparators 138 and 146, respectively. Comparator 138 compares the value of ATEvidence to a previously defined OAT threshold 136. If ATEvidence is greater than the OAT threshold 136, an OAT detection signal 140 is generated.

Comparator 146 compares the value of AFEvidence to a previously defined AF threshold 144. If AFEvidence is greater than the AF threshold 144, an AF detection signal 148 is generated. The OAT threshold 136 and the AF threshold 144 are selected such that the respective comparisons made by comparators 138 and 146 are sensitive and specific to the detection of OAT and AF, respectively.

In a study performed to optimize the two-dimensional histogram dimensions and the parameter set for cluster signature metrics used for OAT and AF detection, the greatest sensitivity and specificity for detection of AF was found using a time interval T of 2 minutes during which ($\delta$RR$_i$, $\delta$RR$_{i-1}$) points are acquired and stored in the histogram and during which scale medians are determined. The optimal histogram dimensions for greatest sensitivity and specificity for AF detection were a histogram range of 500 ms in all axial directions divided into bins of 25 ms in each direction with an NSRmask of 75 ms. Using these settings, sensitivity and specificity of OAT and AF detection were tested for a range of regularity thresholds and a range of OAT thresholds. Optimized thresholds resulted in specificity and sensitivity of 90% or greater for AT/AF burden measurement. The regularity threshold, OAT threshold, and AF threshold settings may be selected and optimized based on historical clinical data of selected patient populations or historical individual patient data. The optimal settings may vary from patient to patient.

Figure 10:
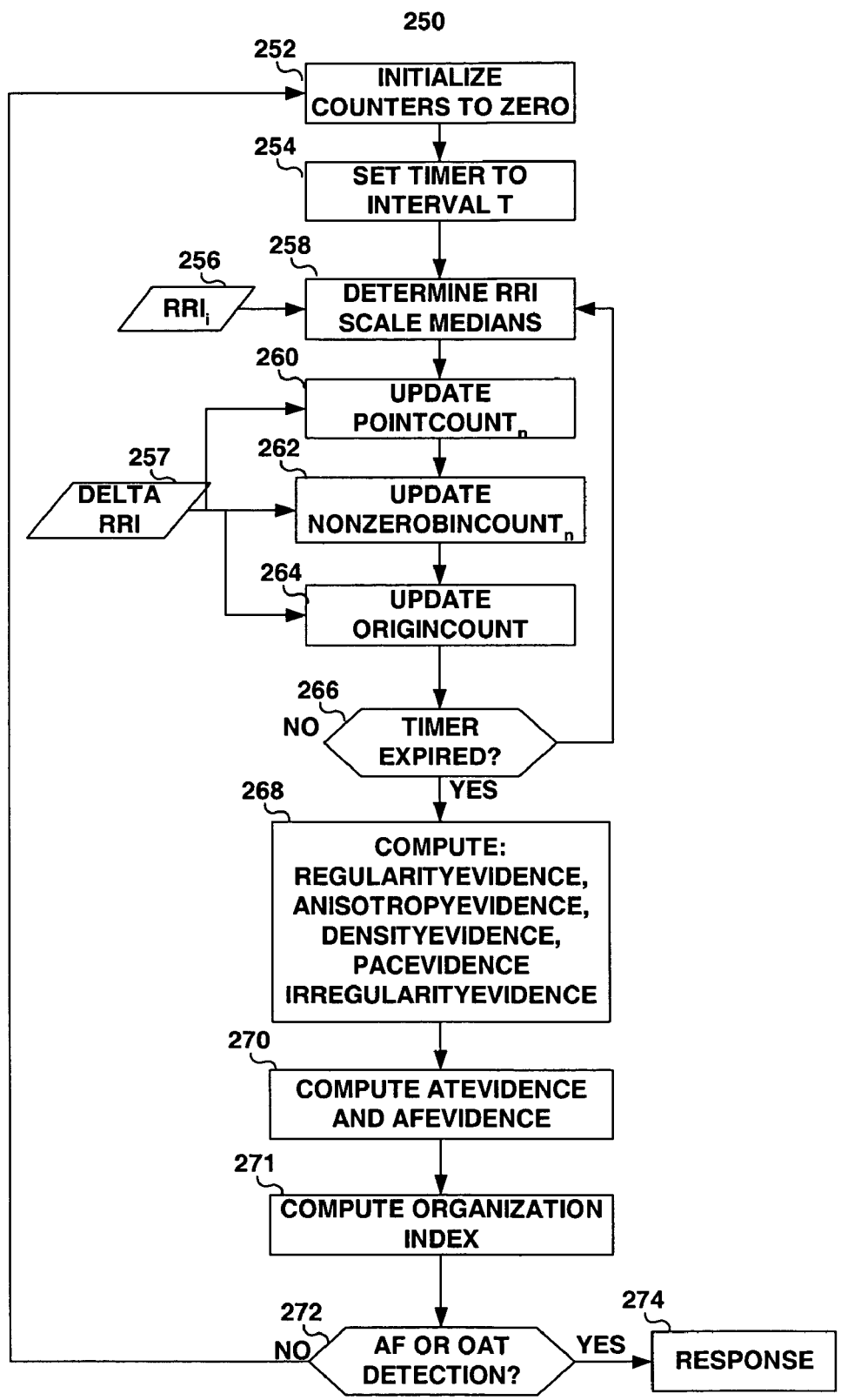
FIG. 10 is a flow chart of a method for using cluster signature metrics for detecting and discriminating cardiac events according to an embodiment of the present invention.

FIG. 10 is a flow chart of a method for using cluster signature metrics for detecting and discriminating cardiac events according to an embodiment of the present invention. Method 250 begins at step 252 by initializing all counters to zero which will be used for counting RRIs, histogram bin counters, PointCount counters, NonZeroBinCount counters, OriginCount counters, and any other counters used in performing the functions described in conjunction with FIG. 6. At step 254, a timer is set to a desired time interval T. The timer is set to 2 minutes in an exemplary embodiment, however, the cluster signature metrics and comparative analyses performed to detect and discriminate OAT and AF can be performed over any desired time interval. Alternatively, a fixed or variable number of VCLs are collected to allow a desired number of ($\delta RR_i$, $\delta RR_{i-1}$) points to be used for AF and OAT detection and discrimination. The number of VCLs obtained may be based on characteristics of the VCL data stream.

At step 256, RRI measurements are provided as input for determining RRI scale medians at step 258. At step 257, $\delta RR_i$ measurements are provided as input for use in updating PointCount$_n$ counters at step 260, NonZeroBinCount$_n$ counters at step 262, and the OriginCount counter at step 264 based on ($\delta RR_i$, $\delta RR_{i-1}$) coordinate locations in a two-dimensional histogram representing the Lorenz plot area as described above.

In practice, computation of the two-dimensional histogram, as shown in FIG. 6, in its entirety is not required in all implementations. In one implementation, bit arithmetic is used to indicate the binary state of each bin. Potentially, only a single bit is required to indicate the bin state (occupied or unoccupied). Using bit arithmetic, the memory requirements for determining cluster signature metrics are reduced. The points in segment 0 need not be counted with the exception of the points in the bin containing the Lorenz plot origin. The NonZeroBinCount$_n$ counters will determine the number of occupied bins in each segment based on the binary state (which requires only a single bit). PointCount will be provided as 12 counters for counting points in each segment 1 through 12.

Hierarchical implementation of Lorenz plot segments may be based on patient history. The rhythm history of the patient may be used to select which segments have the greatest probability of containing ($\delta RR_i$, $\delta RR_{i-1}$) points. For example, segments 9 through 12 as shown in FIG. 1 may be selected for counting points in a patient frequently experiencing OAT with points falling in other segments ignored or counted only as the binary state (occupied or unoccupied) of the histogram bins within those segments. Segments 5 through 8 may be considered next with segments 1 through 4 having the lowest probability of containing points. In some embodiments, the number of bins in lower hierarchical segments may be smaller relative to the number of bins in higher hierarchical segments. For example, segments 1 through 4 may each be assigned a single bin.

The RRI scale medians, PointCount$_n$ counters, NonZeroBinCount$_n$ counters, and the OriginCount counter are updated after each RRI measurement during time interval T. Upon expiration of time interval T, as determined at decision step 266, a number of cluster signature metrics are computed at step 268. The cluster signature metrics can include RegularityEvidence, AnisotropyEvidence, DensityEvidence, PACEvidence, and IrregularityEvidence.

At step 270, metrics of ATEvidence and AFEvidence are computed from the cluster signature metrics computed at step 268. An organization index is optionally computed at step 271. The organization index may be computed as 1 minus the ratio of AFEvidence to ATEvidence. When AT is highly organized, as in AFL, the organization index is close to 1. When AT is highly disorganized, as in AF, the organization index is close to 0. The organization index may be useful in selecting therapies or monitoring a disease state.

In another embodiment the organization index is computed as a weighted sum of OriginCount, RegularityEvidence, AnisotropyEvidence, DensityEvidence, and IrregularityEvidence. An exemplary embodiment would employ weighting factors of {1, 1, 1, 1, –2} respectively for the above named metrics. In yet another embodiment the Histogram counters are used to compute the maximum count in any bin in each segment. The organization index is then computed as the sum of the maximum counts for each segment. Threshold comparisons of ATEvidence, AFEvidence and RegularityEvidence are used at step 272 for detecting AF or OAT. The various threshold values used for comparing to a cluster signature metric for AF and OAT detection are not limited to constant values. In one embodiment the threshold values for detecting the onset of OAT or AF, detecting a transition from OAT to AF, and detecting the offset of OAT and AF may be defined differently. In another embodiment, a threshold value could also be defined as a function of VCL or changes in VCL, and/or one or more cluster signature metrics. For example, a threshold value could be auto-adjusting based on the value of one or more cluster signature metrics or based on the median VCL measured for the current time interval.

If neither AF or OAT are detected based on the threshold comparisons, method 250 returns to step 252 to reset all counters to zero and start a new time interval, T. In case both AFEvidence and ATEvidence exceed associated detection thresholds, the organization index may be used to discriminate between AF and OAT at decision step 272. The organization index is compared to a threshold to determine if the detected arrhythmia is an organized AT (like AFL) or AF.

Thus, AF or OAT detections can be made after each time interval T if cluster signature metrics meet the threshold comparison criteria for AF or OAT detection. Alternatively, AF or OAT detections can be made after any selected number of time intervals. For example, cluster signature metrics can be computed after each time interval, T. After a desired number of time intervals have passed, an OAT/AF decision is made based on a logic that cluster signature metrics computed for X out of Y blocks are required to meet the threshold criteria for OAT or AF detection. Similar logic can be applied for detecting a transition from OAT to AF and the offset of OAT or AF.

If AF or OAT is detected at decision step 272, a response is provided at step 274. Appropriate responses may include storing the detection result, computing an AT/AF burden, generating a report of OAT/AF detections and AT/AF burden and other relevant data, generating an alarm signal, or delivering, withholding, or adjusting a therapy. Delivered or adjusted therapies may include a drug therapy, a cardiac stimulation therapy or a neurostimulation therapy. For example, in response to OAT or AF, appropriate anti-tachyarrhythmia therapies may be delivered. Other types of cardiac stimulation may be withheld upon OAT or AF detection such as extra systolic stimulation. Drug therapies that may be adjusted include anti-arrhythmics and anti-coagulants.

In general, an N-dimensional histogram can be used to numerically represent a Lorenz plot of N time series of $\delta RR$ points. The two-dimensional histogram represents two time series of $\delta RR$ points, $\delta RR_i$ and $\delta RR_i$ delayed by one, or $\delta RR_{i-1}$. In an N-dimensional evaluation, the time series can include $\delta RR_i$, $\delta RR_{i-1}$, $\delta RR_{i-2}$, $\delta RR_{i-3}$, . . . $\delta RR_{i-N-1}$. Cluster signature metrics computed from the N-dimensional histogram representing N time series of $\delta RR$ values are used to evaluate the correlation between the N time series. The ability to predict the next $\delta RR$ point based on the previous $\delta RR$ points indicates a degree of correlation exists which provides evidence of OAT. During AF, no correlation of $\delta RR$ points, hence no predictability, exists. More generally the methods described here can be used to compute the correlation or coherence between any number of time series using only indexing, counting, adds, subtracts and bit shift operations ideally suited for a device with limited computational capacity and battery power. Another two time series example is the heart rate as one time series and blood pressure as the second time series.

Figure 11:
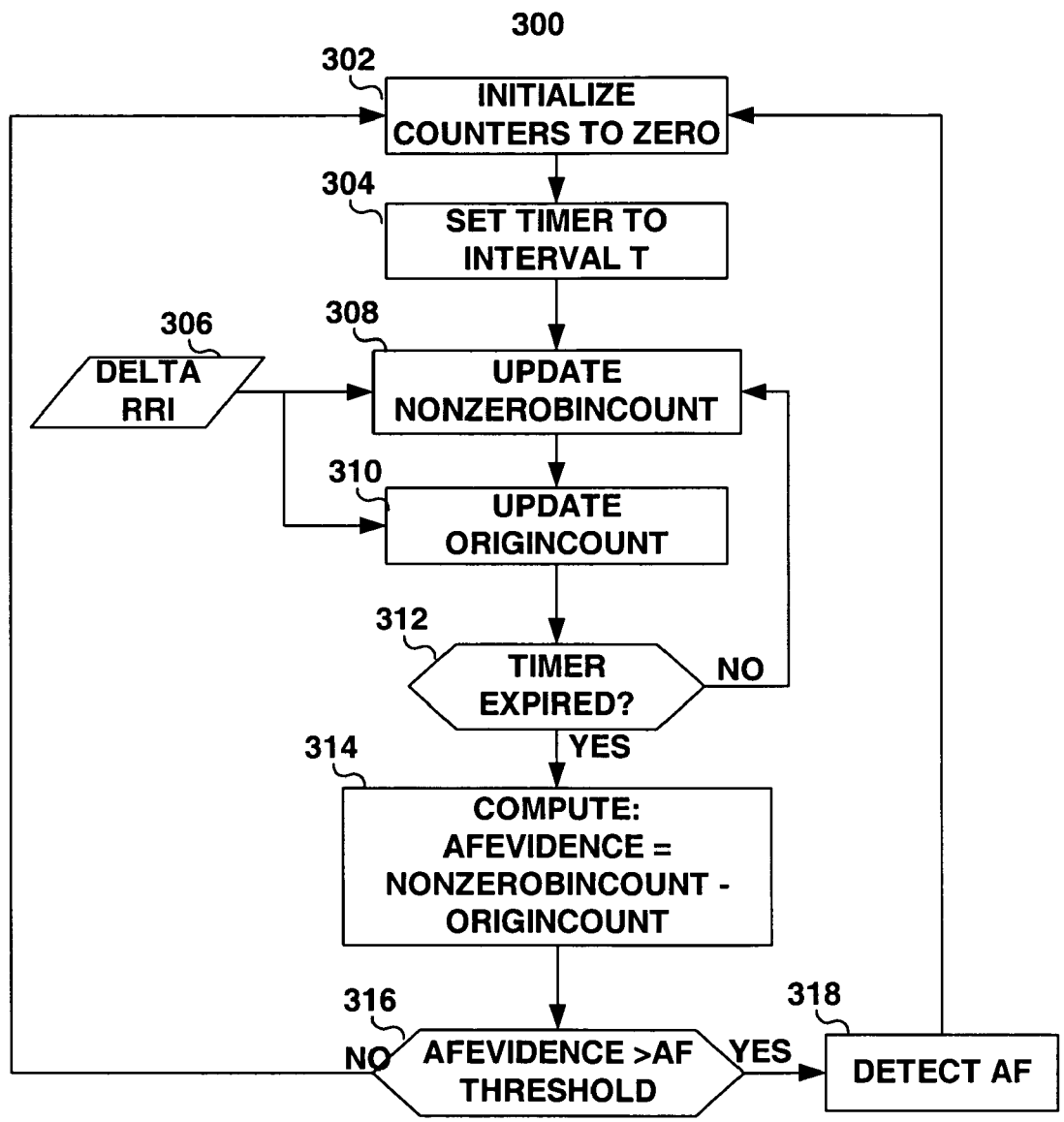
FIG. 11 is a flow chart of a method for using cluster signature metrics for detecting a cardiac event according to an embodiment of the present invention.

FIG. 11 is a flow chart of a method for using cluster signature metrics for detecting a cardiac event according to an embodiment of the present invention. In a simplified embodiment for using cluster signature metrics for AF detection only, segments 1 through 12 may be merged as a single segment. A NonZeroBinCount counter will count the number of occupied bins falling outside segment 0. Only points falling within the bin containing the origin, in segment 0, will be counted by an OriginCount counter. Other points within segment 0 need not be counted.

As such, at step 302, all counters are initialized to 0, and at step 304 a timer is set to a selected time interval T, such as 2 minutes. At step 306, $\delta RR_i$ data is provided as input for updating the NonZeroBinCount counter at step 308 and the OriginCount counter at step 310. In a two-dimensional histogram, histogram bin counts are updated based on the ($\delta RR_i$, $\delta RR_{i-1}$) point for the present ventricular cycle. The NonZeroBinCount counter is increased by one at step 308 if the ($\delta RR_i$, $\delta RR_{i-1}$) falls into any bin outside segment 0 that has not been previously occupied. The OriginCount counter is increased by one at step 310 if the ($\delta RR_i$, $\delta RR_{i-1}$) point falls in the origin bin.

In some embodiments, a one-dimensional histogram representation of the Lorenz plot may be substituted for the 2-D histogram. A 1-D histogram of $\delta RR_i$ will be like a projection of the 2-D histogram along either of the axes. The 2-D histogram includes both magnitude and direction of change in 360 degrees, or phase information, relating to a sequence of three RRIs. The 1-D histogram includes magnitude and bi-direction change information for a sequence of two RRIs. The 1-D histogram provides a significant savings in memory requirements, but is similar to the 2-D histogram implementation in computational requirements. In the 1-D histogram implementation, the NonZeroBinCount counter is updated at step 308 for each $\delta RR_i$ point that falls outside a 0 segment (greater than or less than a selected NSRmask) into a 1-D bin that has not been previously occupied. The OriginCount counter is updated for each $\delta RR_i$ point falling within the bin including the origin of the 1-D histogram.

No PointCount counters are required for the 2-D or 1-D implementations of cluster signature metrics for detection of AF only. Points falling into segment 0 but outside the origin count and points falling into previously occupied histogram bins will have no effect on either of the NonZeroBinCount or OriginCount counters.

If the time interval T has not yet expired, as determined at decision step 312, method 300 continues to acquire ($\delta RR_i$, $\delta RR_{i-1}$) points and updating the NonZeroBinCount and OriginCount counters as appropriate. A metric of AFEvidence is computed as the difference between the NonZeroBinCount and OriginCount. If AFEvidence exceeds an AF detection threshold, as determined at decision step 316, an AF detection is made at step 318. A response may be provided upon AF detection as described previously in conjunction with FIG. 10. Method 300 returns to step 302 to reset the counters to zero and start a new time interval T.

Alternatively, a fixed number of VCLs are collected to allow a desired number of $\delta RR_i$ values to be used for detecting AF and discriminating AF from OAT. In one example, 12 $\delta RR_i$ values are collected and analyzed using the same logic described above for detecting AF.

Figure 12:
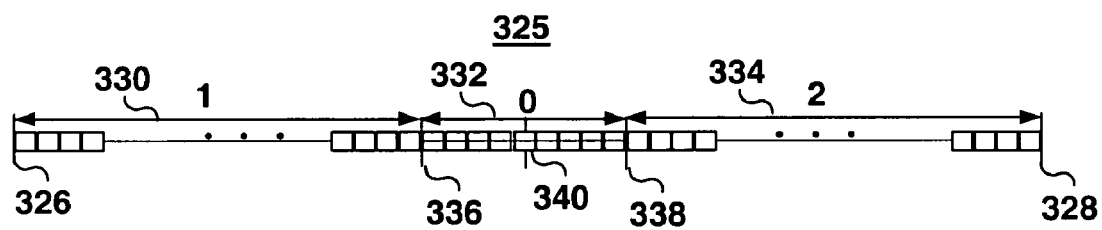
FIG. 12 is a one-dimensional histogram that can be used for storing differences between consecutive RR intervals points in a method for detecting cardiac events according to an embodiment of the present invention.

FIG. 12 is a one-dimensional histogram that can be used for storing differences between consecutive RR intervals points in a method for detecting cardiac events according to an embodiment of the present invention. Three segments 330, 332, and 334 are defined. Segment 0 332 contains the origin bin 340 and extends from −NSRmask 336 to +NSRmask 338. Segment 1 330 extends from the negative range 326, which may be defined by a parameter—Extent, to −NSRmask 336. Segment 1 330 will contain all $\delta RR_i$ points representing a negative change in RRI that is greater than NSRmask. Segment 2 334 extends from +NSRmask 338 to the positive range of the histogram 325 or +Extent 328. Segment 2 334 will contain all $\delta RR_i$ points representing a positive change in RRI that is greater than NSRmask.

Figure 13:
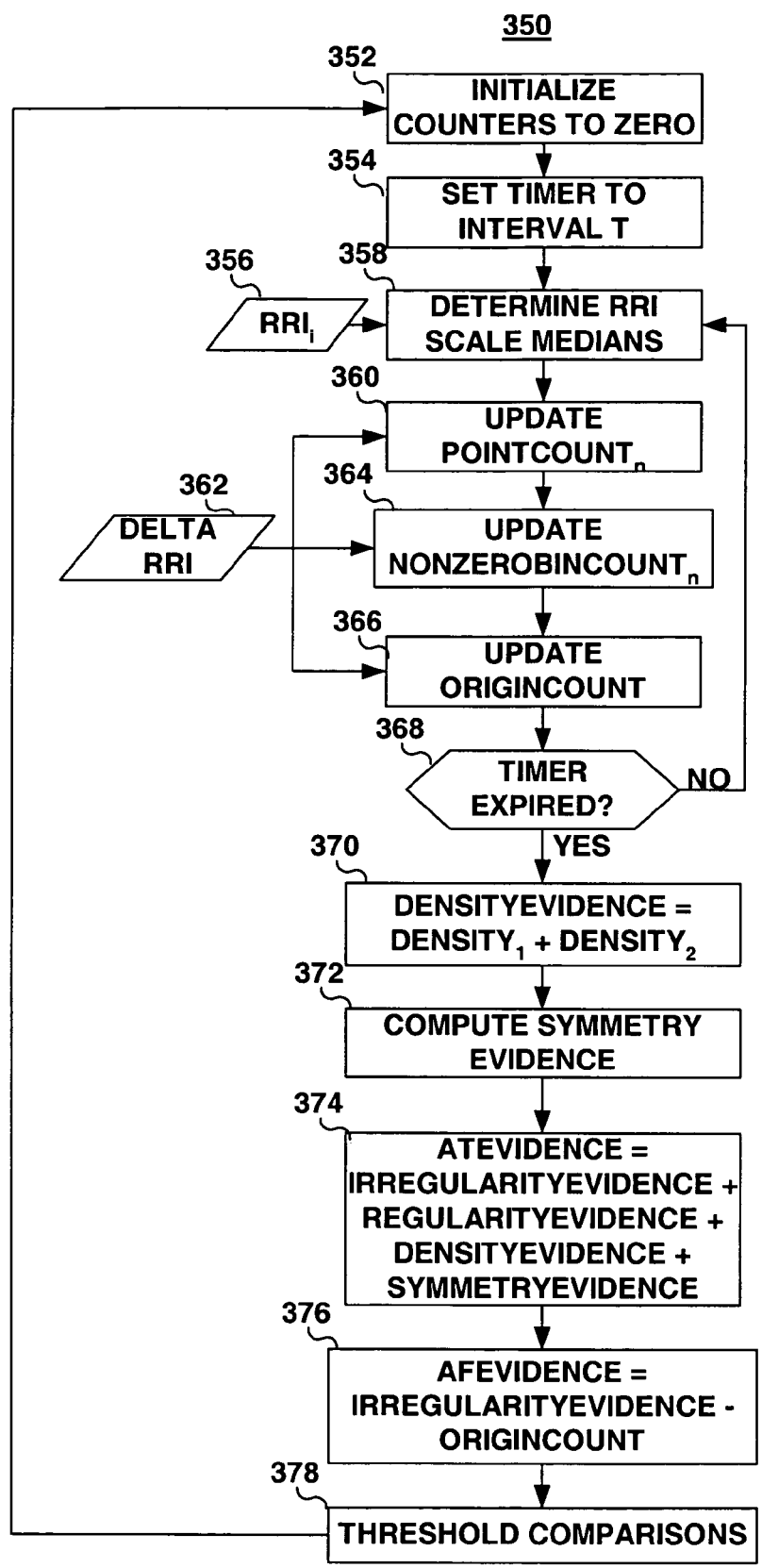
FIG. 13 is a flow chart of a method for detecting cardiac events using a one-dimensional histogram representation of the Lorenz plot according to an embodiment of the present invention.

FIG. 13 is a flow chart of a method for detecting cardiac events using a one-dimensional histogram representation of the Lorenz plot according to an embodiment of the present invention. At step 352, counters used for counting RRI sample numbers, PointCount counters, NonZeroBinCount counters, the OriginCount counter, histogram bin counters and any other counters for executing method 350 are initialized to zero. A timer is set at step 354 to a selected time interval T, typically 2 minutes. At step 356, RRI information is provided to step 358 for determining scaled medians as described previously. RegularityEvidence as computed in the two-dimensional implementation is a one-dimensional concept and can therefore be incorporated in the 1-D implementation. As such, RRI scale medians are determined at step 358 in the same manner as described in conjunction with FIGS. 6, 7 and 8.

At step 362, $\delta RR_i$ information is provided for updating a PointCount counter at step 360, a NonZeroBinCount counter at step 364, and the OriginCount counter at step 366. PointCount counter will count the total number of $\delta RR_i$ points stored each segment 0, 1 and 2 (shown in FIG. 12). NonZero BinCount counter will count the number of occupied bins in each segment 0, 1 and 2. OriginCount counter will count the number of $\delta RR_i$ points falling into the origin bin 340 (shown in FIG. 12).

Since phasic directional information is not available from a 1-D histogram representation, AnisotropyEvidence and DensityEvidence as computed for the 2-D histogram are not available. Substitute cluster signature metrics are computed in the 1-D implementation. After expiration of the timer, as determined at decision step 368, a substitute DensityEvidence metric is computed as the sum of $Density_1$ and $Density_2$. $Density_1$ and $Density_2$ are computed for segments 1 and 2, respectively as the difference between the respective $PointCount_n$ and the $NonZeroBinCount_n$ values, as described previously. DensityEvidence provides a measure of the density of $\delta RR_i$ points falling outside segment 0 and thereby provides an indication of the degree of clustering of points that may be representative of OAT. The 1-D histogram lacks the phasic directional information available in the 2-D histogram, therefore, the DensityEvidence metric provided in the 1-D implementation does not consider only the point clusters typical of OAT (found in the 2-D histogram segments 5 through 12) by excluding point clusters that may be representative of runs of premature beats (found in the 2-D histogram segments of 1 through 4).

SymmetryEvidence is computed at step 372 as a substitute metric for AnisotropyEvidence. During OAT, $\delta RR_i$ points will present a greater degree of symmetry around the origin than during runs of premature beats or during AF. As such, the differences between histogram bins in segment 1 and histogram bins in segment 2 that are equal distances from the origin bin are determined. The maximum absolute value of these differences can be used to determine a SymmetryEvidence metric. In one embodiment, SymmetryEvidence is expressed mathematically as:

$$SymmetryEvidence = 100 - \text{MAX}_{n=NSRmask,Extent} \left| \sum_{i=-n,-NSRmask} i^{th} BinCount_1 - \sum_{j=NSRmask,n} j^{th} BinCount_2 \right|$$

At step 374, ATEvidence is computed for the 1-D implementation as the sum of IrregularityEvidence, RegularityEvidence, DensityEvidence and SymmetryEvidence. IrregularityEvidence is determined as the total NonZeroBinCount counts for segments 1 and 2. At step 376, AFEvidence is computed as the difference between IrregularityEvidence and the OriginCount. This AFEvidence metric is analogous to the AFEvidence metric computed for the method for AF detection only in the 2-D implementation described in conjunction with FIG. 11. AF detection may be made based on recognition of a large number of occupied bins outside segment 0 and a relatively low OriginCount, eliminating the possibility of AFL.

At step 378, the threshold comparisons of AFEvidence, ATEvidence and RegularityEvidence are made for detecting AF or OAT. Each of these cluster signature metrics are compared to a respective, previously defined threshold, AF threshold, OAT threshold, and regularity threshold. If AFEvidence exceeds the AF threshold, AF is detected. If A TEvidence exceed the OAT threshold or RegularityEvidence exceeds the regularity threshold, OAT is detected. After performing the threshold comparisons and making any appropriate detection, method 350 returns to step 352 to reset all counters and start a new time interval, T. An appropriate response to any AF or OAT detection may be made as described previously.

Methods for detecting AF and OAT using cluster signature metrics provide high AF and OAT detection sensitivity and specificity. However, for a patient that is in NSR most of the time, continuously performing CSM methods may unnecessarily consume battery energy. As such, a multi-layered method may be implemented that uses a less computationally demanding base layer algorithm that is highly sensitive in detecting atrial tachyarrhythmias and one or more higher layer algorithms which are highly sensitive and highly specific. The base layer requires less battery energy and memory capacity. The higher layer algorithm(s), which are more computationally demanding, are executed at opportune moments based on the highly sensitive base layer algorithm detections to regain high specificity of the overall performance of the AF/OAT detection method. Such a multi-layered method that conserves battery energy while still providing sensitive and specific AF/OAT detection may incorporate the cluster signature methods described above or any other alternative method for AF and/or OAT detection.

Figure 14:
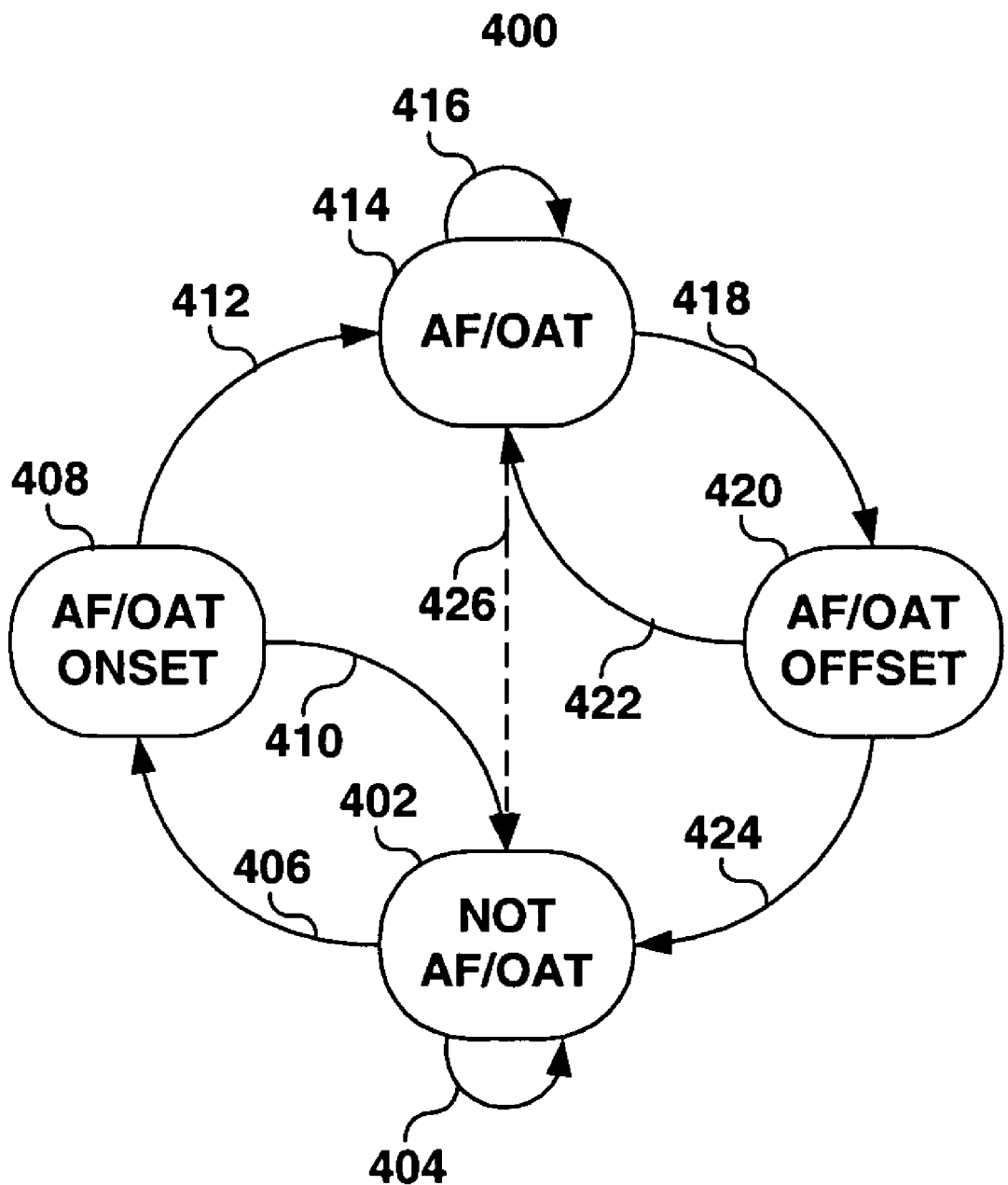
FIG. 14 is a state diagram of a multi-layer method for detecting cardiac events according to an embodiment of the present invention.

FIG. 14 is a state diagram of a multi-layer method for detecting cardiac events according to an embodiment of the present invention. The base layer is designed to be a screening method for determining when the higher layer that is designed to be highly specific and highly sensitive should be performed. The base layer is operating more of the time than the higher layer algorithm, with the higher layer algorithm used to confirm (or maintain) or reject detections made by the base layer algorithm. The bi-layer method that will be described here could be expanded to include additional layers of varying complexity for verifying a condition detected by the base layer.

FIG. 14 illustrates the transition between four possible states: NOT AF/OAT 404, AF/OAT ONSET 408, AF/OAT 414, and AF/OAT OFFSET 420. Beginning in the NOT AF/OAT state 404, the base layer, which requires relatively low or no CPU power and can be done completely in hardware, is monitoring ventricular cycle lengths for the detection of AF/OAT. Base layer algorithms that can be used in bi-layer method 400 will be described below. As long as AF/OAT ONSET detection criteria are not satisfied, the bi-layer method continues to operate in the base layer and remain in the NOT AF/OAT state 402. The base layer algorithm evaluates ventricular cycle length information over a predetermined interval of time, such as 2 minutes. At the end of each time interval, T, the algorithm either transitions to the AF/OAT ONSET state 408 or remains in the NOT AF/OAT state 402 as indicated by loop 404.

When the criteria for detecting AF/OAT ONSET by the base layer algorithm are satisfied, a transition 406 is made to the AF/OAT ONSET state 408. Transition 406 triggers the use of the higher layer algorithm for verifying AF/OAT as detected by the base layer. Thus, in the AF/OAT onset state 408, the higher layer algorithm, which is computationally more complex and generally requires operations performed by a microprocessor, is executed to confirm the AF/OAT detection made by the base layer. If the higher layer algorithm, which is designed to detect AF/OAT with high sensitivity and high specificity, does not detect AF/OAT, a transition 410 is made back to the NOT AF/OAT state 402. The base layer AF/OAT onset detection is rejected by the higher layer algorithm. The transition 410 back to NOT AF/OAT state 402 restores the base layer algorithm operation for monitoring ventricular cycle length information for AF/OAT detection.

If the higher layer algorithm does detect AF/OAT, thereby confirming the AF/OAT onset detection made by the base layer, a transition 412 is made to the AF/OAT detection state 414. Transition 412 to the AF/OAT state 414 triggers the base layer operation for maintaining detection of the AF/OAT episode. The base layer algorithm continues to be performed every time interval, T. If the base layer AF/OAT detection criteria remain satisfied, the algorithm 400 remains in the AF/OAT state 414 as indicated by loop 416. In some embodiments, the higher layer algorithm may be performed periodically or on some intermittent basis during the AF/OAT state 414 for verifying the continued detection of AF/OAT by the base layer algorithm. For example, the higher level algorithm may be performed every other time interval T, every third interval, or at any other designated periodic rate. In some patients, continuous operation of the higher layer algorithm during the AF/OAT state 414 may be desired.

If the AF/OAT detection criteria are no longer satisfied, a transition 418 is made to the AF/OAT OFFSET state 420. Transition 418 to the AF/OAT OFFSET state 420 triggers the operation of the higher layer algorithm for confirming an AF/OAT offset detection by the base layer algorithm. The higher layer algorithm will either confirm the AF/OAT OFFSET detection made by the base layer resulting in a transition 424 back to the NOT AF/OAT state 402 or reject the AF/OAT OFFSET detection made by the base layer resulting in a transition 422 back to the AF/OAT state 414. In either case, method 400 returns to the base layer algorithm for either continuing the detection of AF/OAT in the AF/OAT state 414 or monitoring ventricular cycle length information for a new AF/OAT detection in the NOT AF/OAT state 402.

The periodic performance of the higher layer algorithm during the AF/OAT state 414 for confirming continued detection of AF/OAT could result in a transition 426 directly to the NOT AF/OAT state 402. Generally, decisions made by the base layer algorithm can cause transitions into the AF/OAT ONSET state 408 and AF/OAT OFFSET state 420. Only decisions made by the higher layer algorithm, not the base layer, can cause a transition into the AF/OAT state 414 or into the NOT AF/OAT state 402. The base layer algorithm is designed for screening purposes with a better sensitivity (and perhaps poorer specificity) to detection than the higher layer algorithm. The base layer algorithm thresholds for detection are set such that a very high sensitivity for detection is obtained with little concern for specificity. The higher layer algorithm is used for verifying detections made by the base layer to regain high specificity for detection. Thus, the high sensitivity and specificity of the higher layer algorithm is achieved in a computationally efficient manner. In some embodiments, the multi-layer approach may include additional layers for detecting continuation of an AF/OAT episode, re-detecting AF/OAT, or other aspects of AF/OAT episode detection.

Figure 15:
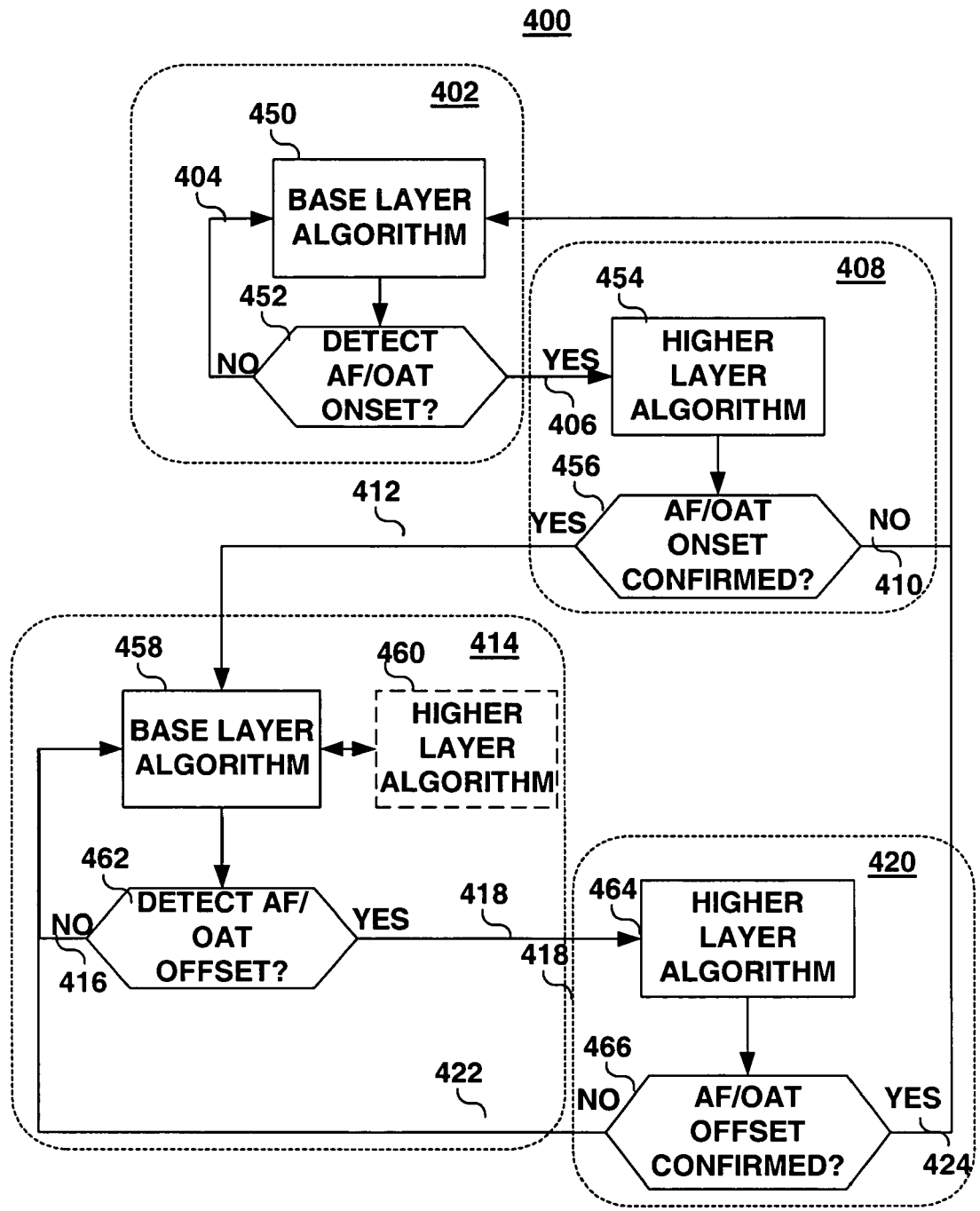
FIG. 15 is a flow chart of transitions between a base layer and a higher layer algorithm in accordance with transition between detection states in the bi-layer method of FIG. 14.

FIG. 15 is a flow chart of transitions between a base layer and a higher layer algorithm in accordance with transition between detection states in the bi-layer method of FIG. 14. Bi-layer method 400 begins in the NOT AF/OAT state 402 executing the base layer algorithm at block 450 during NSR for detecting the onset of AF/OAT. As long as the AF/OAT onset detection criteria are not met, as determined at decision step 452, method 400 repeats the base layer algorithm at block 450 for each time interval T as shown by return loop 404. If AF/OAT onset is detected by the base layer algorithm as determined at decision step 452, transition 406 into the AF/OAT ONSET state 408 initiates the higher layer algorithm at block 454.

If the higher layer algorithm does not confirm the AF/OAT ONSET detection at decision step 456, the transition 410 back to the NOT AF/OAT state 402 restores the base layer algorithm at block 450. If AF/OAT onset is confirmed at decision step 456, the transition 412 to AF/OAT state 414 causes the base layer algorithm to be executed again at step 458 for continuing the AF/OAT detection. Continued detection of AF/OAT can be performed by the base layer algorithm at block 458 or by alternating between the base layer algorithm at block 458 and the higher layer algorithm at block 460. As long as AF/OAT continues to be detected, or AF/OAT offset criteria remain unmet as determined at decision step 462, the base layer algorithm continues to operate at block 458 (with optional periodic higher layer algorithm execution) as indicated by return loop 416.

If AF/OAT offset is detected by the base layer algorithm as determined at decision step 462, the transition 418 to the AF/OAT OFFSET state 420 initiates the higher layer algorithm at block 464 to confirm the termination of the AF/OAT episode. If the AF/OAT offset is not confirmed by the higher layer algorithm, as determined at decision step 466, the transition 422 back to the AF/OAT state 414 causes the base layer algorithm to continue at block 458. If AF/OAT offset is confirmed at decision step 466, transition 424 to the NOT AF/OAT state 402 initiates the base layer algorithm at block 450 for monitoring VCL information for the detection of a new AF/OAT episode.

The base layer algorithm is performed every time interval T during the NOT AF/OAT state 402 and the AF/OAT state 414. The higher layer algorithm is performed over a time interval T upon transition to the AF/OAT ONSET state 408, transition to the AF/OAT OFFSET state 420, and optionally on a periodic or intermittent basis during the AF/OAT state 414. Thus, state transitions can occur at the end of each time interval T. The bi-layer algorithm does not remain in the AF/OAT ONSET state 408 or the AF/OAT OFFSET state 420 for more than one time interval T since the higher layer algorithm will either confirm or reject a decision made by the base layer on a previous time interval T and either revert back to the previous state or transition to a new state. The time interval T over which the base layer and higher layer algorithms evaluate VCL information may be any predefined interval, e.g. 2 minutes. The time interval over which the base layer and higher layer algorithms evaluate VCLs may be the same or different intervals. In some embodiments, the time interval over which the base layer and higher layer algorithms are performed may not be a constant but may vary depending on VCL information.

During the AF/OAT ONSET state 408 and AF/OAT OFFSET state 420 the higher layer algorithm is used to improve the specificity of the AF/OAT onset or offset detection made by the base layer algorithm. In this way, a computationally efficient method for detecting AF/OAT is achieved that is characterized by both high sensitivity (high sensitivity of the higher layer algorithm is not compromised by the base layer algorithm) and high specificity (by the higher layer algorithm). The computational burden will be greatest if the base layer repeatedly detects false positives that are rejected by the higher layer algorithm on every other time interval, i.e. causing a cycling between the NOT AF/OAT state 402 and the AF/OAT ONSET state 408 or cycling between the AF/OAT state 414 and the AF/OAT OFFSET state 420.

The base layer and higher layer algorithms employed by the bi-layer method 400 may be defined according to a variety of embodiments. Generally, the base layer, which can be implemented in hardware, is designed to determine VCL metrics, and compare these metrics to thresholds or other criteria designed to cause AF or OAT detection with a high sensitivity; the goal being a sensitivity approaching 100%. The higher layer algorithm is designed to determine VCL metrics, which can include a number of cluster signature metrics, and compare these metrics to thresholds or other criteria designed to cause AF or OAT detection with a high sensitivity and high specificity. The higher layer algorithm may be embodied as an algorithm that uses cluster signature metrics for AF and/or OAT detection as described previously and generally involves a greater number of metrics and more complex analysis of VCL information than the base layer algorithm to gain greater specificity of the AF/OAT detection.

Other algorithms that use VCL information or variations of the CSM methods described herein can be substituted for the higher layer algorithm. For example, other methods that may be used in bi-layer or multi-layer methods for AF/OAT detection using VCL information are generally disclosed in the previously incorporated U.S. Pat. Publication No. 2004/0092836 A1, by Ritscher et al., and in U.S. Pat. Publication No. 2002/0065473 A1, by Wang et al, hereby incorporated herein by reference in its entirety. In other embodiments the higher layer algorithm may be implemented according to any method that has been designed to detect AF/OAT, for example as described in Tateno K, Glass L. "Automatic detection of atrial fibrillation using the coefficient of variation and density histograms of RR and deltaRR intervals." *Med Biol Eng Comput.* 2001 November;39(6):664-71 or U.S. Pat. Publication No 2005/0165320 by Glass et al., incorporated herein by reference in their entireties. Implementation of the multi-layer method for AF/OAT detection is not limited to using an algorithm that relies on cluster signature methods. The cluster signature methods described herein provide just one example of methods that can be implemented in a higher layer algorithm included a multi-layer method for AF/OAT detection.

Furthermore, the implementation of a multi-layer algorithm which uses a base layer screening algorithm for determining when a higher layer algorithm is needed is not limited to the application of detecting AF/OAT using ventricular cycle length information. Algorithms using other information for detecting AF/OAT, or algorithms using other physiological information for the detection of any other physiological events or conditions, may be incorporated in a multi-layer algorithm operating generally according to the scheme summarized by FIGS. 14 and 15.

Figure 16:
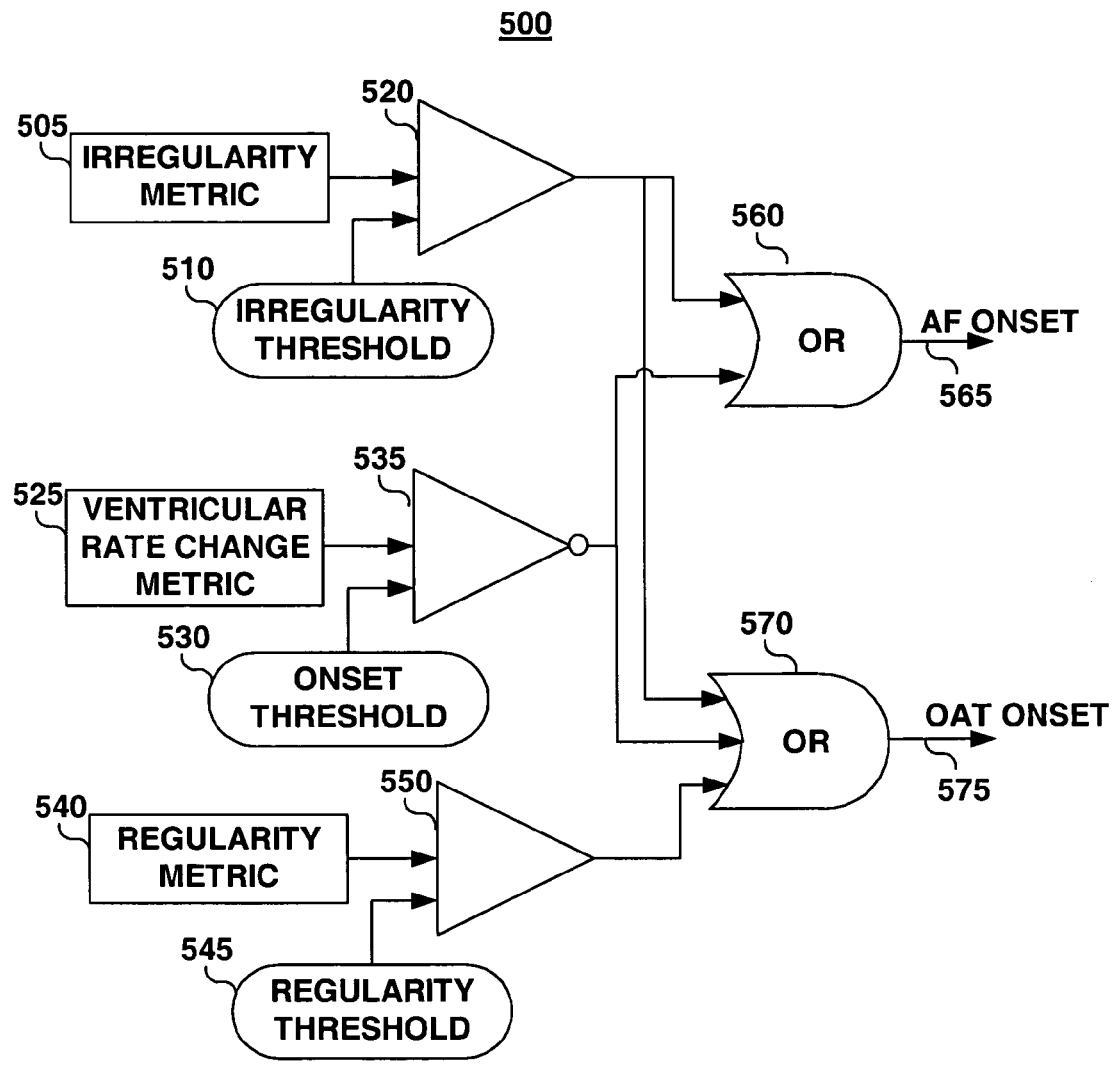
FIG. 16 is a schematic diagram of a base layer algorithm included in a multi-layer method for detecting cardiac events according to an embodiment of the present invention.

FIG. 16 is a schematic diagram of a base layer algorithm included in a multi-layer method for detecting cardiac events according to an embodiment of the present invention. The base layer algorithm 500 uses an irregularity metric 505, a ventricular rate change metric 525 and a regularity metric 540 for detecting AF onset or OAT onset. In one embodiment the irregularity metric 505 may be determined by counting the total number of δRR intervals that are greater than a previously defined NSR threshold. For example, the change in ventricular cycle lengths from one beat to the next during normal sinus rhythm may typically be less than 75 ms, which may be selected as a nominal value for the NSR threshold.

The ventricular rate change metric 525 is used to detect a sudden decrease in ventricular rate that often occurs at the onset of atrial tachycardia or a sudden increase in ventricular rate that can occur at the offset of atrial tachycardia. The ventricular rate change metric can be defined as the median RR interval during the current time interval T or a portion thereof as a percentage or ratio of the median RR interval during the previous time interval T, with the time interval T being smaller than or equal to the time interval over which the higher layer algorithm is executed. For example, the ventricular rate change (VRC) metric may be computed as follows:

$$VRCmetric = \frac{\text{median}\{RR(t-T:t)\} - \text{median}\{RR(t-2T:t-T)\}}{\text{median}\{RR(t-2T:t-T)\}}$$

The irregularity metric 505 and a predefined irregularity threshold 510 are provided as input to comparator 520. The output of comparator 520 will be high if irregularity metric 505 is greater than the irregularity threshold 520. The ventricular rate change metric 525 and a previously defined onset threshold 530 are provided as input to comparator 535. The inverted output of comparator 535 will be high if ventricular rate change metric 535 falls below onset threshold 530. The output from comparators 520 and 535 are provided as input to OR gate 560 for detecting AF onset. If the irregularity metric exceeds the irregularity threshold or the ventricular rate change metric falls below the onset threshold, the output 565 of OR gate 560 will be high indicating AF onset is detected by the base layer algorithm. A higher layer algorithm, such as the method described previously in conjunction with FIG. 6 or any other suitable AF detection method, is performed over the next time interval T for confirming the AF detection.

The regularity metric 540 is used by the base layer algorithm 500 for detecting OAT onset. In one embodiment, the regularity metric 540 is determined as a count of the total number of δRR intervals that are less than a previously defined δRR threshold. One form of OAT, as illustrated by the example in FIG. 3A, is characterized by highly regular VCLs having, for example δRR intervals, less than 20 ms. The regularity metric 540 and a previously defined regularity threshold 545 are provided as input to comparator 550. The output of comparator 550 will be high if regularity metric 540 exceeds regularity threshold 545.

The output of comparators 520, 535, and 550 are provided as input to OR gate 570. The output 575 of OR gate 570 will be high, indicating OAT onset detection, if the irregularity metric 505 exceeds the irregularity threshold 510, or the ventricular rate change metric 525 falls below the onset threshold 530, or the regularity metric 540 exceeds the regularity threshold 550. A higher layer algorithm is performed in response to the OAT onset detection to further evaluate the VCLs over the next time interval T for confirming the OAT detection.

If the irregularity metric is greater than the irregularity threshold, both AF onset and OAT onset are detected. The higher level algorithm is performed to confirm either the AF or OAT detection and reject the other detection, or reject both detections. The irregularity threshold, onset threshold, and regularity threshold are optimized to achieve a high sensitivity, approaching 100%, for AF onset and OAT onset detections. The base layer algorithm 500 is designed to be sensitive but does not need to be highly specific in detecting atrial tachyarrhythmias. High AF/OAT specificity is regained in the design of the higher layer algorithm.

Figure 17:
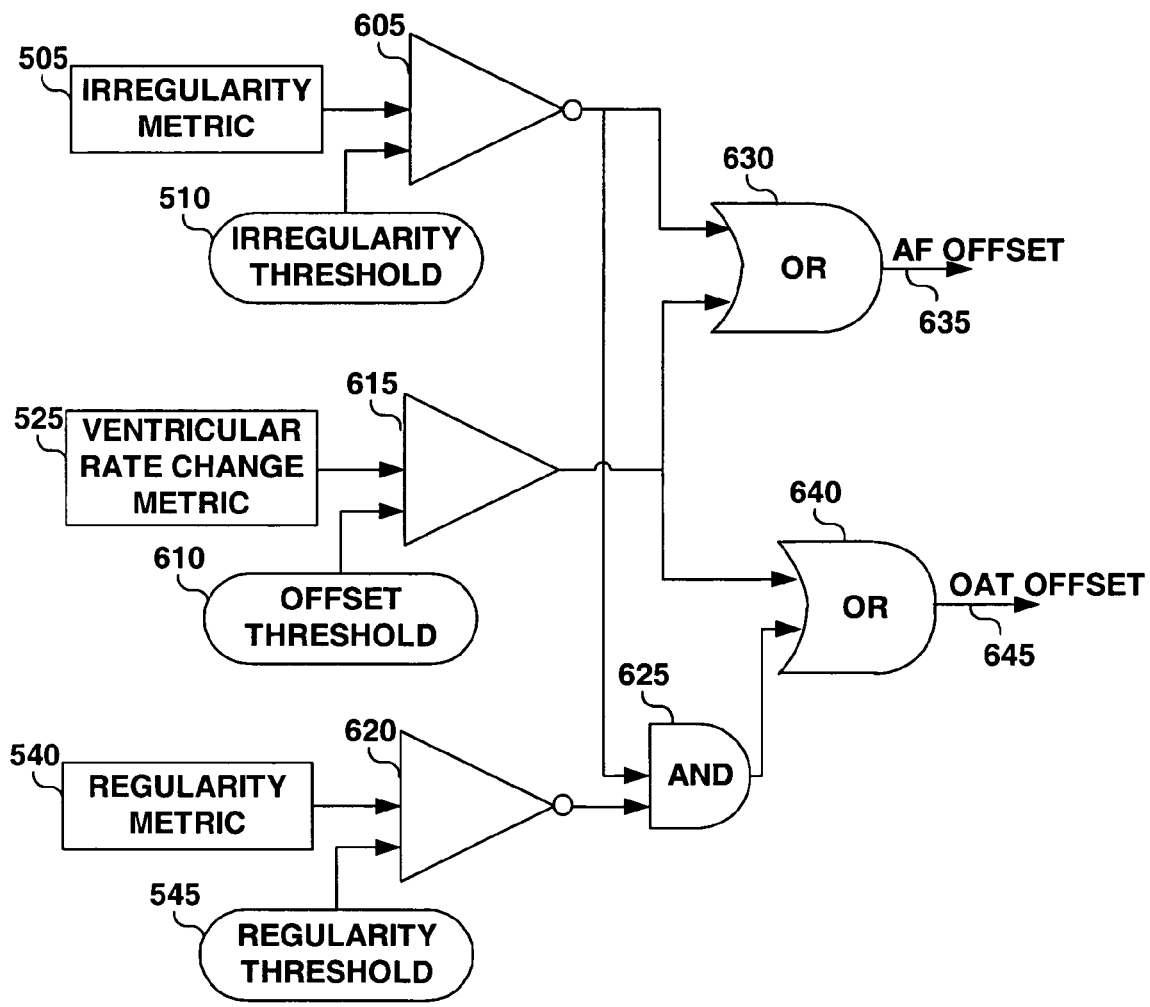
FIG. 17 is a schematic diagram of a base layer algorithm for detecting a cardiac event offset according to an embodiment of the present invention.

FIG. 17 is a schematic diagram of a base layer algorithm for detecting a cardiac event offset according to an embodiment of the present invention. Irregularity metric 605 and irregularity threshold 610 are provided as input to comparator 605. The inverted output of comparator 605 will be high when irregularity metric 505 falls below irregularity threshold 510. Ventricular rate change metric 525 and a previously defined offset threshold 610 are provided as input to comparator 615. The output of comparator 615 will be high if the ventricular rate metric 525 exceeds the offset threshold 620, indicating a sudden ventricular rate increase that can be associated with the offset of atrial arrhythmias.

The outputs of comparators 605 and 615 are provided as input to OR gate 630. The output 635 of OR gate 640 will be high indicating detection of AF offset by the base layer algorithm if the irregularity metric falls below the irregularity threshold or the ventricular rate change metric crosses the offset threshold. A higher layer algorithm is executed in response to the AF offset detection over the next time interval T to verify the NOT AF state. The irregularity threshold values used in detecting onset and in detecting offset may be defined differently.

Regularity metric 540 and previously defined regularity threshold 545 are provided as input to comparator 620. The inverted output of comparator 620 is high if the regularity metric 540 falls below regularity threshold 545. The outputs of comparators 605 and 620 are provided as input to AND gate 625. The output of AND gate 625 will be high when the irregularity metric 505 falls below irregularity threshold 510 and regularity metric 540 falls below regularity threshold 545. The regularity threshold values used in detecting onset and in detecting offset may be defined differently.

The output of AND gate 625 and the output of comparator 615 are provided as input to OR gate 640. If the ventricular rate change metric exceeds the offset threshold or the regularity metric falls below the regularity threshold and the irregularity metric falls below the irregularity threshold, the output 645 of OR gate 640 will be high, indicating OAT offset detection by the base layer algorithm. A higher layer algorithm is executed in response to an OAT offset detection over the next time interval T to confirm a not OAT state.

Figure 18A:
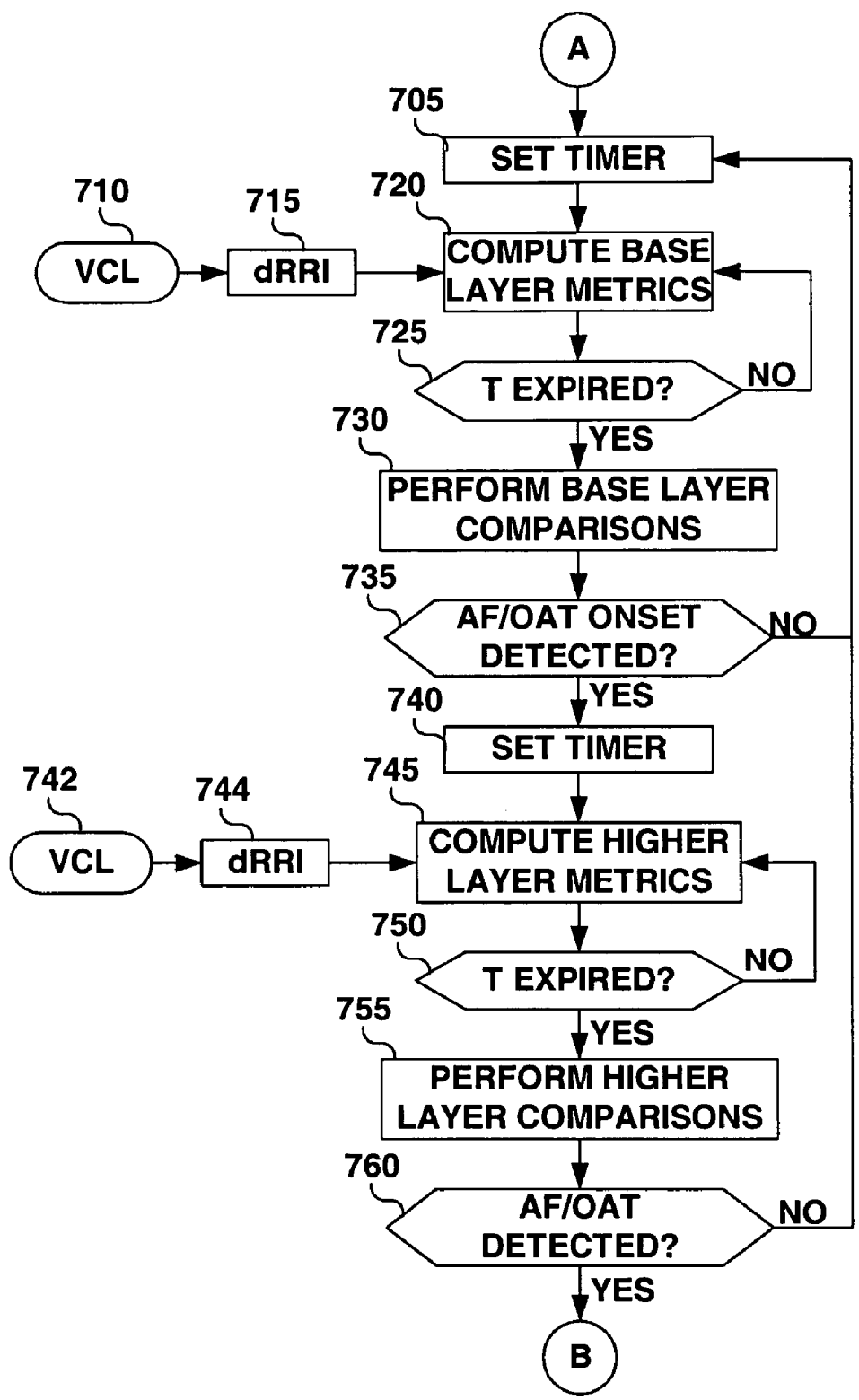
FIGS. 18A and 18B are schematic diagrams of a base layer algorithm and a higher layer algorithm used in a bi-layer method for detecting cardiac events according to an embodiment of the present invention.
Figure 18B:
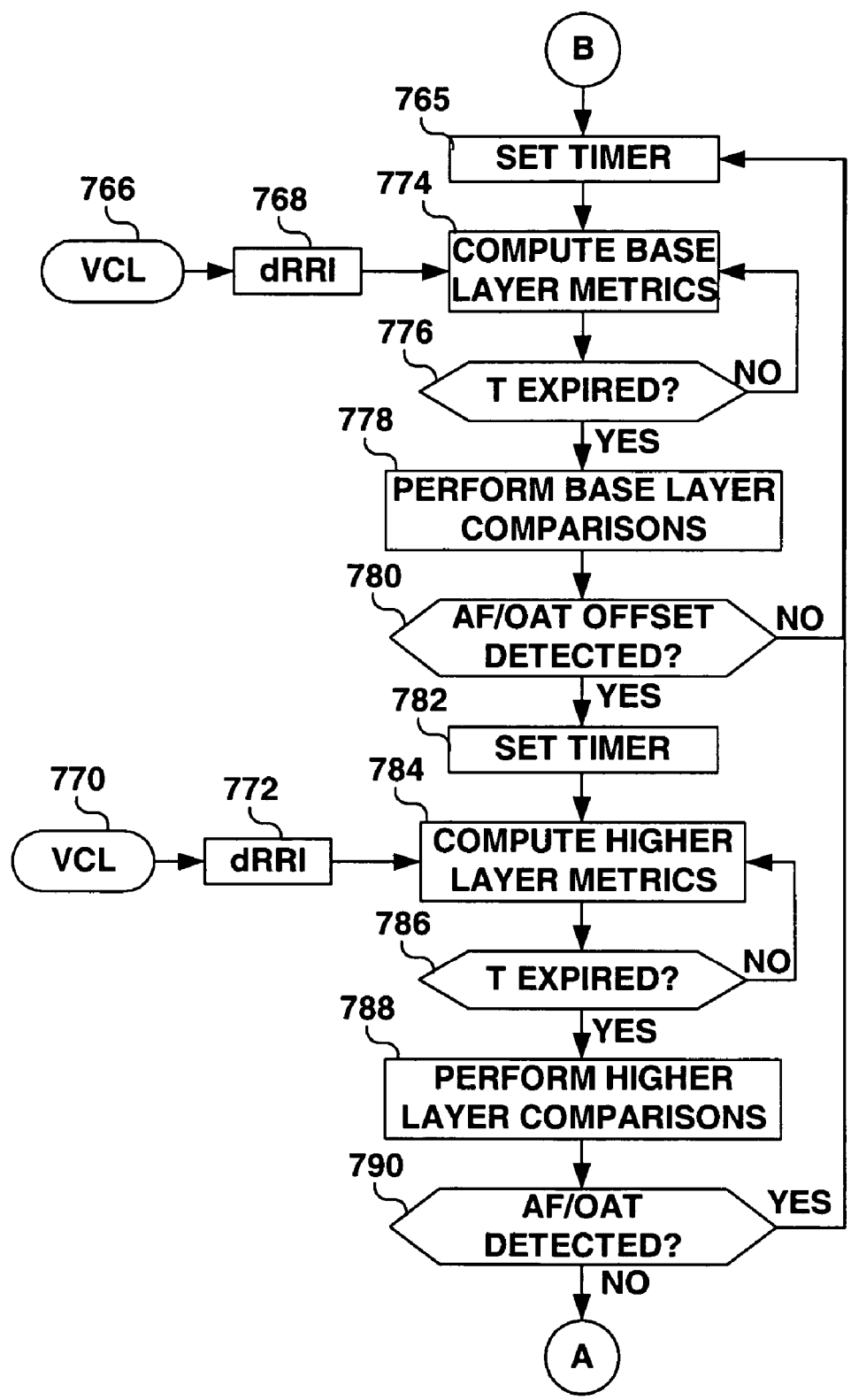

FIGS. 18A and 18B are schematic diagrams of a base layer algorithm and a higher layer algorithm used in a bi-layer method for detecting cardiac events according to an embodiment of the present invention. The base layer algorithm is operating initially for the first time interval T. As such, a timer is set at step 705 to the time interval T, and the base layer metrics are computed using δRR$_i$ data input 715 determined from VCL measurement information 710. Depending on the metrics used by the base layer, metrics may be updated upon each δRR$_i$ input or at the end of the time interval T. Referring to the base layer algorithm shown in FIGS. 16 and 17, a counter counting the δRR intervals greater than NSR Threshold can be operating during the base layer execution.

Upon expiration of the time interval T, as determined at decision step 725, the base layer algorithm evaluates the metrics by comparing the computed metrics to previously defined thresholds. With regard to the base layer algorithm of FIG. 16, an irregularity metric, a ventricular rate change metric and a regularity metric are compared to the corresponding irregularity threshold, onset threshold, and regularity threshold. Based on these comparisons, an AF onset or OAT onset may be detected at decision step 735. If the criteria for detecting AF onset or OAT onset are not met, method 700 returns to step 705 to repeat the base layer algorithm over the next time interval T.

If AF onset or OAT onset detection is made at decision step 735, the timer is set at step 740 to initiate the higher layer algorithm at step 745. In one embodiment, the higher layer metrics are computed at step 745 using δRR$_i$ data input 744 derived from ventricular cycle length information 742 for generating a Lorenz plot histogram and computing a number of cluster signature metrics as described in conjunction with FIG. 6. The higher layer algorithm uses a more detailed Lorenz plot histogram, including multiple segments, for example as illustrated in FIG. 1. Some higher layer metrics are computed or updated after each cardiac cycle and some are computed at the end of the time interval T as described previously in conjunction with FIG. 6.

Upon expiration of time interval T, as determined at decision step 750, the higher layer algorithm evaluates the VCL information by comparing the computed cluster signature metrics to previously determined thresholds. If the higher layer algorithm detects AF or OAT at decision step 760, confirming an AF onset or OAT onset detection made by the base layer algorithm, method 700 proceeds to step 765 (FIG. 18B) for initiating the base layer algorithm in the AF/OAT state. If the higher layer algorithm does not detect AF or OAT at decision step 760, rejecting the AF onset or OAT onset detection made by the base layer, method 700 returns to step 705 to restore operation of the base layer algorithm in the NOT AF/NOT OAT state, to continue monitoring for AF or OAT onset.

At step 765, the time is set to start the next time interval T during which the base layer algorithm computes the base layer metrics using the δRR$_i$ data input 768 derived from VCL information 766. In a similar manner as described above, the base layer metrics are computed at step 774 and after expiration of time interval T, as determined at decision step 776, base layer algorithm comparisons are performed for detecting the offset of the AF or OAT episode. With regard to FIG. 17, the base layer algorithm computes the irregularity metric, ventricular cycle length metric and regularity metric and compares these metrics to the corresponding irregularity threshold, offset threshold, and regularity threshold for detecting AF or OAT offset as described above. The irregularity threshold and regularity threshold used for detecting onset at step 730 and may be defined differently than the irregularity threshold and regularity threshold used for detecting offset at step 778.

If AF/OAT offset is not detected, as determined at decision step 780, method 700 returns to step 765 to repeat the base layer algorithm over the next time interval T. If AF/OAT offset is detected, method 700 proceeds to step 782 for setting the timer to the next time interval T and initiating the higher layer algorithm for confirming the NOT AF/NOT OAT state. At step 784, the higher layer metrics are computed using the δRR$_i$ data input 772 derived from ventricular cycle length information 770 in the manner described above.

Upon expiration of time interval T, the higher layer algorithm evaluates the higher layer metrics by performing comparisons to predetermined thresholds. If the higher layer algorithm detects AF or OAT, method 700 returns to step 765 to restore the base layer algorithm for continuing to monitor for AF/OAT offset. If the higher layer algorithm does not detect AF or OAT, thereby confirming the base layer offset detection, method 700 returns to step 705 to restart the base layer algorithm on the next time interval T for monitoring for a new AF/OAT onset.

As noted previously, the higher layer algorithm may be executed continuously or periodically during AF/OAT to maintain a high sensitivity and specificity of continued detection of the AF/OAT episode. In some embodiments, the higher layer algorithm may be used continuously during the AF/OAT state. In particular, the higher layer algorithm may be used intermittently or continuously in patients having paroxysmal AF.

The multi-layer methods described herein generally refer to executing the base layer and higher layer algorithms over a specified time interval T. It is recognized that these algorithms may alternatively be performed over a specified number of detected RR intervals. In some embodiments, a minimum number of δRR$_i$ data points is defined which are required for computing the cluster signature or other ventricular cycle length metrics. A time interval is specified over which δRR$_i$ data points are acquired and if the minimum number of data points is not obtained during one time interval, data acquired during that time interval may be discarded. The minimum number of time intervals may not be reached due to R-wave undersensing. In other embodiments, a time interval during which the minimum number of required δRR$_i$ data points is not reached may be concatenated with a subsequent time interval such that slow ventricular rhythms are not discarded from the VCL evaluation for AF/OAT detection.

Thus, methods have been described which provide for AF and OAT detection using VCL information without requiring an atrial signal. These methods can be beneficial in monitoring and therapy applications in which discrimination of ventricular tachycardias from supraventricular tachycardias are important. Moreover, discrimination of AF from OAT provides a more accurate diagnostic view of the patient for managing therapies and monitoring disease state. Embodiments described in detail herein are provided to illustrate exemplary embodiments of the invention and are not intended to be limiting with regard to the following claims.

What is claimed is:

1. A method of identifying a cardiac event, comprising:
   detecting sensed events using a first detection format in a first state during detection of other than the cardiac event;
   advancing from the first state to a second state corresponding to suspending the detecting using the first detection format and detecting sensed events using a second format different from the first detection format in response to the first detection format determining the sensed events correspond to the cardiac event while in the first state;

advancing from the second state to the first state in response to the second detection format determining the sensed events do not correspond to the cardiac event while in the second state;

advancing from the second state to a third state in response to the second detection format determining the sensed events correspond to the cardiac event while in the second state, the third state corresponding to detecting sensed events using the first detection format;

advancing from the third state to a fourth state in response to the sensed events being determined not to correspond to the cardiac event while in the third state, the fourth state corresponding to suspending the detection using the first format and detecting sensed events using the second detection format;

advancing from the fourth state to the third state in response to the sensed events being determined to correspond to the cardiac event while in the fourth state; and advancing from the fourth state to the first state in response to the sensed events being determined not to correspond to the cardiac event while in the fourth state.

2. The method of claim 1, further comprising detecting sensed events using the first detection format and the second detection format while in the third state.

3. The method of claim 2, further comprising alternating between detecting sensed events using the first detection format and detecting sensed events using the second detection format while in the third state.

4. The method of claim 1, wherein the detecting using the second detection format is performed within a predetermined time period, the method further comprising advancing from the second state to one of the first state and the third state and from the fourth state to one of the third state and the first state within the predetermined time period.

5. The method of claim 4, wherein the predetermined time period corresponds to a predetermined number of detected RR-intervals.

6. The method of claim 1, wherein the second detection format comprises:
   determining a plurality of cycle lengths associated with sensed cardiac signals;
   determining differences between consecutive cycle lengths of the determined plurality of cycle lengths;
   determining cluster signature metrics in response to the determined differences;
   generating a plot corresponding to the determined differences; and
   determining a number of the determined differences that are located within a plurality of segments of the plot defined by a range of magnitudes and phases relative to an origin of the plot and corresponding to patterns associated with the cardiac event.

7. The method of claim 1, wherein the first detection format includes a first metric corresponding to a first change in cycle lengths, a second metric corresponding to one of a decrease in ventricular rate and an increase in ventricular rate, and a third metric corresponding to a second change in cycle lengths.

8. The method of claim 7, wherein the cardiac event is determined to correspond to onset of atrial fibrillation in response to one of the first metric and the second metric, and to onset of organized atrial tachycardia in response to one of the first metric, the second metric and the third metric.

9. The method of claim 7, wherein the cardiac event is determined to correspond to onset of atrial fibrillation in response to one of the first metric and the second metric, and to onset of organized atrial tachycardia in response to one of the first and the third metric and the second metric.

10. A method of identifying a cardiac event, comprising:
   detecting sensed events using a first detection format in a first state during detection of other than the cardiac event;
   advancing from the first state to a second state corresponding to suspending the detecting using the first detection format and detecting sensed events using a second format different from the first detection format in response to the first detection format determining the sensed events correspond to the cardiac event while in the first state;
   advancing from the second state to the first state in response to the second detection format determining the sensed events do not correspond to the cardiac event while in the second state;
   advancing from the second state to a third state in response to the second detection format determining the sensed events correspond to the cardiac event while in the second state, the third state corresponding to detecting sensed events using the first detection format;
   advancing from the third state to a fourth state in response to the sensed events being determined not to correspond to the cardiac event while in the third state, the fourth state corresponding to suspending the detection using the first format and detecting sensed events using the second detection format;
   advancing from the fourth state to the third state in response to the sensed events being determined to correspond to the cardiac event while in the fourth state; and
   advancing from the fourth state to the first state in response to the sensed events being determined not to correspond to the cardiac event while in the fourth state, wherein the second detection format comprises:
   determining a plurality of cycle lengths associated with sensed cardiac signals;
   determining differences between consecutive cycle lengths of the determined plurality of cycle lengths;
   determining cluster signature metrics in response to the determined differences;
   generating a plot corresponding to the determined differences; and
   determining a number of the determined differences that are located within a plurality of segments of the plot defined by a range of magnitudes and phases relative to an origin of the plot and corresponding to patterns associated with the cardiac event, and wherein the first detection format includes a first metric corresponding to a first change in cycle lengths, a second metric corresponding to one of a decrease in ventricular rate and an increase in ventricular rate, and a third metric corresponding to a second change in cycle lengths.

11. The method of claim 10, further comprising detecting sensed events using the first detection format and the second detection format while in the third state.

12. The method of claim 11, further comprising alternating between detecting sensed events using the first detection format and detecting sensed events using the second detection format while in the third state.

13. The method of claim 11, wherein the detecting using the second detection format is performed within a predetermined time period, the method further comprising advancing from the second state to one of the first state and the third state and from the fourth state to one of the third state and the first state within the predetermined time period.

14. The method of claim 13, wherein the predetermined time period corresponds to a predetermined number of detected RR-intervals.

15. The method of claim 10 wherein the cardiac event is determined to correspond to onset of atrial fibrillation in response to one of the first metric and the second metric, and to onset of organized atrial tachycardia in response to one of the first metric, the second metric and the third metric.

16. The method of claim 10, wherein the cardiac event is determined to correspond to onset of atrial fibrillation in response to one of the first metric and the second metric, and to onset of organized atrial tachycardia in response to one of the first and the third metric and the second metric.

* * * * *